(12) United States Patent
Norenberg

(10) Patent No.: US 10,744,214 B2
(45) Date of Patent: Aug. 18, 2020

(54) METHOD OF DIAGNOSING AND/OR MONITORING THERAPY OF ATHEROSCLEROSIS

(71) Applicant: STC.UNM, Albuquerque, NM (US)

(72) Inventor: Jeffrey P. Norenberg, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 16/065,393

(22) PCT Filed: Dec. 28, 2016

(86) PCT No.: PCT/US2016/068840
§ 371 (c)(1),
(2) Date: Jun. 22, 2018

(87) PCT Pub. No.: WO2017/117199
PCT Pub. Date: Jul. 6, 2017

(65) Prior Publication Data
US 2018/0369430 A1  Dec. 27, 2018

Related U.S. Application Data

(63) Continuation of application No. 62/271,573, filed on Dec. 28, 2015.

(51) Int. Cl.
| | | |
|---|---|---|
| *A61K 51/04* | (2006.01) | |
| *A61K 49/10* | (2006.01) | |
| *A61K 47/22* | (2006.01) | |

(52) U.S. Cl.
CPC ...... *A61K 51/0482* (2013.01); *A61K 51/0453* (2013.01); *A61K 47/22* (2013.01); *A61K 49/106* (2013.01)

(58) Field of Classification Search
CPC ......... A61K 51/05; A61K 49/10; A61K 51/04
See application file for complete search history.

(56) References Cited

U.S. PATENT DOCUMENTS

| | | |
|---|---|---|
| 2005/0010038 A1 | 1/2005 | Liu |
| 2007/0048216 A1 | 3/2007 | Norenberg |
| 2011/0117014 A1* | 5/2011 | Norenberg ......... A61K 51/0497 424/1.65 |

OTHER PUBLICATIONS

Marcus R. Makowski et al., MR Imaging of the Arterial Vessel Wall: Molecular Imaging from Bench to Bedside, Radiology, vol. 269(1), 35-51. (Year: 2013).*
Arai, Y., et al., Long-Term Effect of Lipid-Lowering Therapy on Atherosclerosis of Abdominal Aorta in Patients with Hypercholesterolemia: Noninvasive Evaluation by a New Image Analysis Program. Angiology, 2002. 53(1): p. 57-68.
Blackwell DL, L.J., Clarke TC, Summary health statistics for U.S. adults: National Health Interview Survey. National Center for Health Statistics, 2012. Vital Health Stat 10(260).
Bykov, A.T., et al., [Early diagnostics, prophylaxis, and non-pharmacological treatment of the preclinical stages of atherosclerosis and arterial hypertension]. Vopr Kurortol Fizioter Lech Fiz Kult, 2015. 92(5): p. 18-21.
Jie Sun, M., et al., Subclinical Carotid Atherosclerosis: Short-term Natural History of Lipid-rich Necrotic Core—A Multicenter Study with MR Imaging. 2013.
Choi, S.Y. and G.S. Mintz, What have we learned about plaque rupture in acute coronary syndromes? Curr Cardiol Rep, 2010. 12(4): p. 338-43.
Ten Kate, G.L., et al., Molecular imaging of inflammation and intraplaque vasa vasorum: a step forward to identification of vulnerable plaques? J Nucl Cardiol, 2010. 17(5): p. 897-912.
Hansson, G.K., A.K. Robertson, and C. Soderberg-Naucler, Inflammation and atherosclerosis. Annu Rev Pathol, 2006. 1: p. 297-329.
Imanaka-Yoshida, K., Tenascin-C in Cardiovascular Tissue Remodeling. Circulation Journal, 2012. 76(11): p. 2513-2520.
Nakata, Y. and N. Maeda, Vulnerable atherosclerotic plaque morphology in apolipoprotein E-deficient mice unable to make ascorbic Acid. Circulation, 2002. 105(12): p. 1485-90.
Johnson, J., et al., Plaque rupture after short periods of fat feeding in the apolipoprotein E-knockout mouse: model characterization and effects of pravastatin treatment. Circulation, 2005. 111(11): p. 1422-30.
Sasaki, T., et al., A simple method of plaque rupture induction in apolipoprotein E-deficient mice. Arterioscler Thromb Vasc Biol, 2006. 26(6): p. 1304-09.
Dimastromatteo, J., et al., In vivo molecular imaging of atherosclerotic lesions in ApoE-/-mice using VCAM-1-specific, 99mTc-labeled peptidic sequences. J Nucl Med, 2013. 54(8): p. 1442-9.
O'Brien, K.D., Vascular Cell Adhesion Molecule-1 Is Expressed in Human Coronary Atherosclerotic Plaques. The American Socciety for Clinical Investigation, 1993.
Sadeghi, M.M., The pathobiology of the vessel wall: implications for imaging. J Nucl Cardiol, 2006. 13(3): p. 402-14.
Willem J. M. Mulder, F.A.J., Zahi A. Fayad, Matthias Nahrendorf, Imaging and Nanomedicine in Inflammatory Atherosclerosis. Atherosclerosis, 2014. 6(239).
Sadeghi, M.M., et al., Imaging atherosclerosis and vulnerable plaque. J Nucl Med, 2010. 51 Suppl 1: p. 51S-65S.

(Continued)

*Primary Examiner* — Michael G. Hartley
*Assistant Examiner* — Jagadishwar R Samala
(74) *Attorney, Agent, or Firm* — Henry D. Coleman; R. Neil Sudol

(57) ABSTRACT

The present invention is directed to novel non-invasive diagnostic took to dispose numerous disease states and/or conditions. The presets invention, represents a clear advance in the art which presently relies on tissue biopsy for diagnoses of these disease states. The novel imaging probe is capable of detecting infected cells, as well tissue. The methods described herein are able to diagnose, treat and/or monitor the therapy of numerous diseases and conditions including atherosclerosis, atherothrombosis, cerebral vascular disease, cerebral ischemia, cerebral infarct and meningitis as well as pneumonitis, pericarditis, multiple sclerosis, lupus erythematosus and pancreatitis, among others.

20 Claims, 28 Drawing Sheets

(56) References Cited

OTHER PUBLICATIONS

Van Leeuwen, M., et al., Accumulation of myeloperoxidase-positive neutrophils in atherosclerotic lesions in LDLR-/- mice. Arterioscler Thromb Vasc Biol, 2008. 28(1): p. 84-9.

Hong, S.N. et al. Atherosclerotic biomarkers and aortic atherosclerosis by cardiovascular magnetic resonance imaging in the Framingham Heart Study. J Am Heart Assoc, 2013. 2(6): p. e000307.

Horst, E., et al., Expression of the leucocyte Horst integrin LFA-1 (CD11a/CD18) and its ligand ICAM-1 (CD54) in lymphoid malignancies is related to lineage derivation and stage of differentiation but not to tumor grade. Leukemia, 1991. 5(10): p. 848-53.

Yee, N.K., Self-Regeneration of Stereocenters: A Practical Enantiospecific Synthesis of LFA-1 Antagonist BIRT-377. 2000.

Kelly, T.A., Cutting Edge: A Small Molecule Antagonist of LFA-1-Mediated Cell Adhesion. The Journal of Immunology, 2015.

Shaw, S.K., et al., Coordinated redistribution of leukocyte LFA-1 and endothelial cell ICAM-1 accompany neutrophil transmigration. J Exp Med, 2004. 200(12): p. 1571-80.

Silvola, J.M.U., et al., Uptake of (68)gallium in atherosclerotic plaques in LDLR(-/-)ApoB(100/100) mice. Ejnmmi Research, 2011. 1.

Rahul B. Poria, J.P.N., Tamara L. Anderson,2 Jack Erion, Carston R. Wagner, Jeffrey B. Arterburn, and Richard S. Larson6, Characterization of a Radiolabeled Small Molecule Targeting Leukocyte Function-Associated Antigen-1 Expression in Lymphoma and Leukemia. Cancer Biotherapy & Radiopharmaceuticals, 2006.vol. 21 (5) , 418-427.

Herrington, W., et al., Epidemiology of Atherosclerosis and the Potential to Reduce the Global Burden of Atherothrombotic Disease. Circ Res, 2016. 118(4): p. 535-46.

Burtea, C., et al., Development of a magnetic resonance imaging protocol for the characterization of atherosclerotic plaque by using vascular cell adhesion molecule-1 and apoptosis-targeted ultrasmall superparamagnetic iron oxide derivatives. Arterioscler Thromb Vasc Biol, 2012. 32(6): p. e36-e48.

Collins, R.G., et al., P-Selectin or intercellular adhesion molecule (ICAM)-1 deficiency substantially protects against atherosclerosis in apolipoprotein E-deficient mice. J Exp Med, 2000. 191(1): p. 189-94.

Anderson, M.E. and T.J. Siahaan, Targeting ICAM-1/LFA-1 interaction for controlling autoimmune diseases: designing peptide and small molecule inhibitors. Peptides, 2003. 24(3): p. 487-501.

Wang, X.J., et al., Efficient synthesis of a small molecule, nonpeptide inhibitor of LFA-1. Org Lett, 2010. 12(19): p. 4412-5.

Vestweber, D., Adhesion and signaling molecules controlling the transmigration of leukocytes through endothelium. Immunological Reviews, 2007.

Tabdanov, E., et al., Regulation of Immune Synapse Cytoskeleton Mechanics by CD3 and LFA1. Biophysical Journal, 2011. 100(3): p. 34-35.

Riou, L.M., et al., Pre-clinical and clinical evaluation of nuclear tracers for the molecular imaging of vulnerable atherosclerosis: an overview. Curr Med Chem, 2009. 16(12): p. 1499-511.

Perales, J.L.G., Blood volume analysis by radioisotopic dilution techniques: State of the art. Applied Radiation and Isotopes, 2015. 96: p. 71-82.

Otsuki, H., et al., Comparison of iron-59, indium-111, and gallium-69 transferrin as a macromolecular tracer of vascular permeability and the transferrin receptor. J Nucl Med, 1989. 30(10): p. 1676-85.

Moos, M.P., et al., The lamina adventitia is the major site of immune cell accumulation in standard chow-fed apolipoprotein E-deficient mice. Arterioscler Thromb Vasc Biol, 2005. 25(11): p. 2386-91.

Ramot, Y., et al., Clinical and pathological manifestations of cardiovascular disease in rat models: the influence of acute ozone exposure. Inhal Toxicol, 2015. 27 Suppl 1: p. 26-38.

Katakami, N., Utility of Carotid Wall Shear Stress as a Predictor of Coronary Atherosclerosis. J Atheroscler Thromb, 2016. 23(3): p. 290-1.

Meng, H., et al., [Feasibility of targeted magnetic resonance imaging on visualizing tenascin-C expression in atherosclerosis plaque in high-fat diet fed ApoE(-/-) mice]. Zhonghua Xin Xue Guan Bing Za Zhi, 2016. 44(4): p. 342-7.

Mata, P., et al., [Familial combined hyperlipidemia: consensus document]. Semergen, 2014. 40(7): p. 374-80.

Abd El-Aziz, T.A. And R.H. Mohamed, LDLR, ApoB and ApoE genes polymorphisms and classical risk factors in premature coronary artery disease. Gene, 2016.

* cited by examiner

FIG 1A. MVE INDUCED CARDIOPULMONARY INFLAMMATION

FIG1B. END DIASTOLIC/SYSTOLIC VOLUMES DECREASED BY MVE

SERUM %IA/gr

HIGH FAT vs. NORMAL CHOW %IA/gr

LIVER %IA/gr

HEART %IA/gr

AORTIC %IA/gr per group

RED BLOOD CELL/WHITE BLOOD CELL %IA/gr

WHOLE BLOOD COMPONENTS ISOLATION IN OZONE vs. FILTERED AIR EXPOSURE POST $^{68}$Ga-DANBIRT INCUBATION

A

B

24hr PI AUTORADIOGRAPHY IMAGES SHOWING ROI FROM TARGET TISSUES

FIGURE 13

Table 1 [$^{111}$In] In-DANBIRT animal study design

| ApoE-/- mice with C57BL/6 background, n:16 | | | |
|---|---|---|---|
| | Normal Diet | High Fat Diet (HFC) | Total |
| SPECT/CT, Bio distribution | 4 | 4 | 8 |
| Serum lipids | 4 | 4 | 8 |
| Total | 8 | 8 | 16 |

| Sprague Dawley male rats, n:6 | | |
|---|---|---|
| | Filtered Air | Ozone (1ppm) |
| Ozone vs Filtered Air 4-hr Exposure | 3 | 3 |

| ApoE-/- mice with C57BL/6 background, n:8 | | |
|---|---|---|
| | Normal Diet | High Fat Diet |
| 3D Autoradiography | 4 | 4 |

FIGURE 14

TABLE 2 UPLC METHOD GRADIENT WITH FLOW RATE

|    | Time (min) | % Solvent B | Flow (ml/min) |
|----|------------|-------------|---------------|
| 1  | 0.00       | 50.0        | 0.800         |
| 2  | 0.15       | 50.0        | 0.800         |
| 3  | 3.00       | 60.0        | 0.800         |
| 4  | 5.00       | 80.0        | 0.800         |
| 5  | 7.00       | 100.0       | 0.800         |
| 6  | 7.50       | 100.0       | 0.800         |
| 7  | 8.00       | 0.0         | 0.800         |
| 8  | 8.50       | 0.0         | 0.800         |
| 9  | 8.60       | 50.0        | 0.800         |
| 10 | 9.00       | 50.0        | 0.800         |

FIGURE 15

Table 3. SPECT/CT imaging parameters

| Topogram/CT | | | | SPECT | |
|---|---|---|---|---|---|
| Scan Range (mm) | ~30 | Projections | 360 | Pinhole Size (mm) | 1.4 |
| | | | | Projections/Rotation | 360 |
| Tube voltage (kVp) | 65 | Pitch | 1.5 | Time/Projection (s) | ~75 |
| Exposure time (sec) | 500 | Acquisition time (min:sec) | 3:00 | Acquisition time (min:sec) | ~50:00 |
| Tube current (µA) | 123 | | | Energy window (keV) | 158-183, 226-263 |

Radiolabeled DANBIRT in vitro stability

Biodistribution analysis of [$^{111}$In] In-DANBIRT on ApoE$^{-/-}$ mice after 8 weeks of dietary assessment Percentage weight gain per week from baseline weight of ApoE$^{-/-}$ mice after 8 weeks of dietary assessment Serum total cholesterol and triglyceride level quantification in ApoE-/- mice per dietary group Histologic analysis of OCT frozen subaortic leaflet atherosclerotic lesions Immunohistochemistry of OCT frozen subaortic leaflet atherosclerotic lesions Radiolabeled DANBIRT uptake in isolated blood components post 4-hour exposure to ozone 3hr [¹¹¹In] In-DANBIRT SPECT/CT imaging

METHOD OF DIAGNOSING AND/OR MONITORING THERAPY OF ATHEROSCLEROSIS

RELATED APPLICATIONS AND GRANT SUPPORT

The present application is a United States national phase patent application based upon international patent application number PCT/US16/68840 of international filing date Dec. 28, 2016, which claims the benefit of priority of provisional application U.S. 62/271,573 of identical title, filed Dec. 28, 2015, the entire contents of said two applications which is incorporated by reference herein.

This invention was made with government support under grant nos. P30CA118100-06 and ES0014639 awarded by the National Institute of Health (NIH). The government has certain rights in the invention.

FIELD OF THE INVENTION

The present invention is directed to diagnosing and imaging tissue suspected of or known to affected by atherosclerosis, atherothrombosis and related disease states and conditions. The present invention can be used to diagnose the presence and extent of atherosclerotic tissue, atherosclerotic plaque in tissue (including vascular atherosclerotic lesions) in blood vessels and/or cardiovascular tissue (especially cardiopulmonary tissue) of a patient suspected of having atherosclerosis and/or atherthrombosis. The present invention can be used to determine the existence and extent of atherosclerosis (especially inflammatory leukocyte presence and accumulation in vascular atherosclerotic plaque) which can be assessed to determine a patient's risk of a cardiovascular event, allowing steps to be taken to treat the atherosclerosis before an untoward cardiovascular event in a patient occurs. The imaging probe and diagnostic/therapy monitoring method is capable of detecting atherosclerotic tissue, as well as the level and extent of atherosclerosis, especially including atherosclerotic plaque and/or atherothrombosis in tissues, especially blood vessels, including often arteries and/or arterioles and including heart, aortic arch, descending aorta, carotids, femoral, profunda femoris, renal, hypogastric, iliac (common, interior and exterior), popliteal fossa, peroneal, anterior tibial artery, posterior tibial artery, anterior dorsalis pedis, abdominal aorta, celiac artery, gastric artery, hepatic artery, splenic artery, subclavian artery, axillary artery, brachial artery, radial artery, ulnar artery, thoracic aorta, superior mesenteric artery and inferior mesenteric artery of a patient. The present invention may also be used to diagnose and/or monitor therapy of a number of conditions which heretofore have been difficult to diagnose and/or monitor, including diseases of the brain such as cerebral vascular disease, cerebral ischemia, cerebral infarct and meningitis as well as pneumonitis, pericarditis, multiple sclerosis, lupus erythematosus and pancreatitis. The present invention results in a significant advance and step forward in the diagnosis and treatment of infectious disease using the non-invasive molecular imaging techniques. Thus, in the present invention, the existence of a disease state may be diagnosed as well as the extent of disease (useful in monitoring therapy). Accordingly, the present invention may be used to diagnose disease and related conditions, including hard-to-diagnose disease states and conditions, including infections and to assist in therapy of infections by monitoring therapy and the response of the disease to therapy. Compounds according to the present invention may be used as diagnostic tools for a number of conditions and diseases states as well as therapeutic agents for treating such conditions and disease states.

BACKGROUND OF THE INVENTION

Atherosclerosis is a chronic cardiovascular disease common in patients exhibiting hypercholesterolemia[1]. The number of adults with diagnosed heart disease has been estimated to be 26.6 million (11.3%) in the US[2], with more than half of those patients are associated with or are potentially causal with respect to atherosclerotic disease. Prevention and early diagnosis of atherosclerotic disease complications is a top priority in modern medicine[3], as early lifestyle and medical interventions can slow the rate of atheroma development and avert adverse cardiovascular sequelae. Early stage diagnosis is challenging, however; symptoms often become clinically evident only at late stages where complete prevention is no longer viable[4]. As vascular disease progresses, the inflammatory and remodeling process also evolves, and the plaque can become unstable or vulnerable to erosion or rupture, which in turn initiates life-threatening thrombotic outcomes. The penultimate pathological event, plaque rupture, is identified due to thrombogenic processes and immune cell infiltration[5]. Histological changes in a vulnerable plaque such as thin fibrous cap, intraplaque hemorrhage and/or a lipid-rich necrotic chore (LRNC) are present in ~80% of ruptured plaques, but such manifestations require a prolonged and variable time for progression[6].

Cardiovascular inflammation[7] and remodeling due to atherogenic progression[8] have also been identified as leading causes of plaque instability, despite incomplete understanding of these complex process[9]. ApoE$^{-/-}$ mouse model on HFD exhibits rapid development of atheromatous plaques[10], with features and stages that mirror those of the human disease[11]. Early stages of atherosclerosis typically include altered homeostasis and activation of the vascular endothelium, typified by a loss of nitric oxide generation and increased expression of chemokines and adhesion molecules [12], which is evident in the ApoE$^{-/-}$ model[13]. The role of T cells and monocytes recruited to the plaques and perivascular regions have been studied extensively in the vascular immune response, but the ability to identify intraplaque presence and extent of specific leukocyte subtypes is mostly limited to invasive and/or post-mortem or post-resection imaging[14-16]. The role of intraplaque neutrophil accumulation has been recently identified as a focus point in atherosclerotic plaque vulnerability[17]. Elevation of typical biomarkers for disease progression is exploited by molecular imaging[18], which is limited at the same lime because of the low specificity of current diagnostic tools.

DANBIRT was developed by chemical repurposing of BIRT 377, which is a specific therapeutic agent for leukemia and lymphoma, as it targets LFA-1 expressed on both B and T-cells[19]. Developed targeted ligand, DANBIRT, is a small non-ionic compound that acts as an allosteric inhibitor of LEA 1[20]. The importance of LFA-1 is critical for the initiation and impulse of a vascular immune response to injury[21]. LFA-1 is involved in specific interaction with Intracellular Adhesion Molecule-1 (ICAM-1) in endothelial cells by which transmigration is achieved[22]. Radiolabeling DANBIRT using $^{111}$In (FIG. 1) allows co-localization of the radiopharmaceutical in cardiovascular and immune tissues[23].

BRIEF DESCRIPTION OF THE INVENTION

In the present invention, an agent for imaging tissues, in particular tissue infected or inflamed are disclosed. Compounds of the present invention have the chemical formula I:

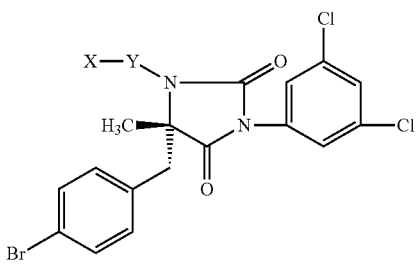

Where Y is a chemical linker which links the nitrogen (as indicated in the structure) to a chelate group which can be attached at various positions of the chelate or a tricarbonyl complex X, wherein X incorporates or complexes with a radioisotope. In preferred aspects of the invention, Y is an optionally substituted $C_1$-$C_{10}$ hydrocarbyl (including an optionally substituted aryl group), preferably an optionally substituted alkyl group, for example a —$(CH_2)_n$Z— group, where n is from 1 to 6 and Z is O, NR or N(R)—$CH_2CH_2$—O, where R is H or a $C_1$-$C_5$ alkyl (preferably H) or Z is a keto (C=O) group, an amide group, a urethane group, a S(O)w group where w is from 0 to 4 (i.e., a sulfide, sulfoxide, sulfone, sulfonate or sulfate group), a phosphonate group or a phosphate group and X is a chelate group in which a radioisotope is incorporated or complexed. In certain preferred aspects, Y is a —$(CH_2)_n$NH— group, where n is from 1 to 6, preferably from 2 to 4, preferably 4 and X is a polyaminocarboxylic macrocycle, preferably 1,4,7,10-tetraazacyclododecane-1,4,7,10-tetraacetic acid (DOTA).

In other aspects of the invention, Y is a linker comprising a $C_1$-$C_{10}$, preferably a $C_3$-$C_8$ substituted hydrocarbyl group (which is bonded to the nitrogen of the dioxoimidazolyl group through a keto group) containing two amino groups or two sulfur groups which are linked with the tricarbonyl compound X which incorporates or complexes to the radioisotope. In certain aspects, the preferred linker contains a dithiahexyl group or a diaminohexyl or diaminobutyl group. In another aspect, the linker may be derived from lysine (linked to the dioxoimidazolinyl group through the carboxylic acid moiety of lysine). Chemical linkage of the linker to the dioxoimidazolinyl group may be through a carbonyl group, alkylene group or other group capable of being linked to the nitrogen of the dioxoimidazolinyl group.

Preferred compounds according to the present invention may be represented by the chemical structure:

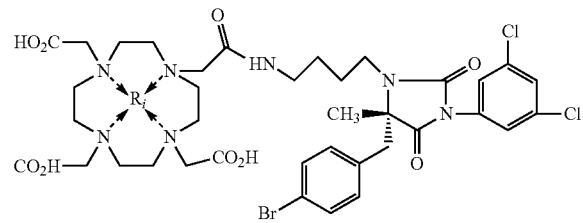

Where Ri is a radioisotope as otherwise described herein below, more preferably $^{212}$Bi, $^{213}$Bi, $^{212}$Pb, $^{177}$Lu, $^{225}$Ac, $^{68}$Ga, $^{67}$Ga, $^{66}$Ga, $^{86}$Y, $^{90}$Y, or $^{111}$In. In particularly preferred aspects, Ri are $^{111}$In ($^{111}$In$^{3+}$) or $^{68}$Ga ($^{68}$Ga$^{3+}$). It is noted that compounds according to the present invention exhibit a favorable bioavailability to tissues which have been infected with a microbial infection, thus providing a ready means by which the infection may be diagnosed and/or monitored for therapeutic success or failure. This favorable bioavailability is also evidenced in certain tissues, which allows the methods of the present application to be particularly suitable for diagnosing and/or monitoring. In the above chemical formula, the carboxylate groups may be complexed with the radioisotope as depicted below:

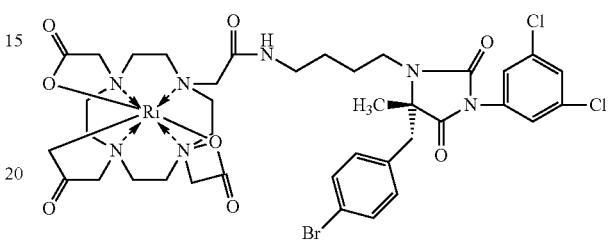

Radioisotopes are selected based on the physical half life, the decay mode (alpha, beta, auger, gamma, X-ray) and the energy of the radioisotope. Exemplary radioisotopes for use in the present invention include, for example, $^{86}$Y, $^{90}$Y, $^{111}$In, $^{177}$Lu, $^{225}$Ac, $^{209}$Bi, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{89}$Zr, $^{203}$Pb, $^{209}$Pb, $^{212}$Pb, $^{166}$Ho, $^{153}$Pm, $^{201}$Tl, $^{188}$Re, $^{186}$Re, $^{99m}$Tc. In certain aspects of the present invention, preferred radioisotopes include, for example, $^{212}$Bi, $^{213}$Bi, $^{212}$Pb, $^{177}$Lu, $^{225}$Ac, $^{68}$Ga, $^{67}$Ga, $^{66}$Ga, $^{86}$Y, $^{90}$Y, or $^{111}$In, more preferably $^{213}$Bi, $^{377}$Lu, $^{111}$In, $^{68}$Ga, even more often, $^{68}$Ga and $^{111}$In, among others. $^{111}$In and $^{68}$Ga are preferred for use in the present invention because the incorporation of these radioisotopes into the basic chemical structure, especially in compounds containing a DOTA chelate moiety results in a compound having favorable bioavailability characteristics after administration to a patient. Many radioisotopes are used in the present invention preferably in cationic form (e.g., tricationic form).

Methods of diagnosing and/or monitoring the treatment of diseases or conditions, especially infectious or inflammatory diseases or conditions as set forth herein represent a preferred embodiment of the invention. In this method, an effective amount of one or more compounds according to the present invention (which amount may vary as a function of the intensity of the image provided, the particle emitted from the radionuclide of the compound and the weight and age of the patient) is administered to a patient in need thereof to diagnose a condition or disease state or to monitor and/or assess the treatment of the condition or disease state. Disease states or conditions which may be diagnosed or treated by the present invention include, for example: atherosclerosis, especially the buildup and/or extent of atherosclerotic plaque in tissues, especially blood vessels, including often arteries and/or arterioles and including heart, aortic arch, descending aorta, carotids, femoral, profunda femoris, renal, hypogastric, iliac (common, interior and exterior), popliteal fossa, peroneal, anterior tibial artery, posterior tibial artery, anterior dorsalis pedis, abdominal aorta, celiac artery, gastric artery, hepatic artery, splenic artery, subclavian artery, axillary artery, brachial artery, radial artery, ulnar artery, thoracic aorta, superior mesenteric artery and inferior mesenteric artery of a patient, atherothrombosis which may occur in those same tissues, diseases of the brain such as cerebral vascular disease, cerebral ischemia, cerebral infarct and meningitis as well as pneumonitis, pericarditis, multiple sclerosis, lupus erythematosus and pancreatitis.

In the diagnostic method according to the present invention, a compound according to the present invention is administered to a patient. Evidence of a disease state or condition of the tissue to be diagnosed and its relevance to disease (for example, from elevated expression of LFA-1/CAM receptors) in tissue of said patient is made through standard well-known nuclear imaging techniques, especially radiation (radionuclide) imaging, including scintigraphic imaging, in which an image(s) taken from a patient is/are compared to a standard, which may be an image from normal, uninfected tissue or an image or images front infected tissue at various stages of infection, is indicative of a disease state or condition in the tissue of the patient. In general, elevated levels of radiation emanating from a diagnosed tissue is evidence of elevated LFA-1/CAM receptor activity and indicative of a disease state or condition w herein these receptors are found at elevated levels and a disease state or condition occurs. It has recently been discovered that the present method is applicable to additional disease states and conditions as set forth herein, including atherosclerosis, atherosclerotic plaque in tissues, especially blood vessels, including often arteries and/or arterioles and including heart, aortic arch, descending aorta, carotids, femoral, profunda femoris, renal, hypogastric, iliac (common, interior and exterior), popliteal fossa, peroneal, anterior tibial artery, posterior tibial artery, anterior dorsalis pedis, abdominal aorta, celiac artery, gastric artery, hepatic artery, splenic artery, subclavian artery, axillary artery, brachial artery, radial artery, ulnar artery, thoracic aorta, superior mesenteric artery and inferior mesenteric artery of a patient, atherothrombosis, cerebral vascular disease, cerebral ischemia, cerebral infarct and meningitis as well as pneumonitis, pericarditis, multiple sclerosis, lupus erythematosus and pancreatitis. Thus, the present invention may be used to diagnose the existence and/or severity of a disease state, as well as response of a disease state or condition to therapy. This is done by imaging tissue which is infected or suspected of being infected to develop one or more images and then comparing the image(s) with a standard image or images from normal tissue and/or infected tissue.

Diagnosis of a disease state and/or condition and/or monitoring of treatment of a disease state/condition in tissue by methods according to the present invention represent principal aspects of the present invention. This method optionally comprises the step of modifying treatment of the disease state or condition in the event that the monitoring evidences that therapy should be modified.

The present invention represents the use of a novel, leukocyte function-associated antigen-1 (LFA1)-targeted small-molecule radioligand for non-invasive imaging of inflammation and immune cell activity in vascular disease, cardiovascular disease, stroke, angina, myocardial infarct. This small-molecule probe can be labeled with radionuclide or optically active moieties to allow PET, SPECT, optical, bioluminescent imaging.

Atherosclerotic plaque has been identified as an important mechanism of vascular disease, including cardiovascular disease. Inflammation and immune cell activity in atherosclerotic plaque is believed to play an important role in vascular homeostasis. In atherosclerotic disease, inflammation and immune cell activity, especially leukocytes and/or lymphocytes have been associated with plaque friability and instability. The breakup of unstable atherosclerotic plaque is known to cause embolic events that may lead to the release of emboli or thrombus formation. Thus, the detection of vulnerable plaque is an important prognostic factor in assessing the risk of embolic vascular occlusion, which can cause myocardial infarct and stroke.

LFA1 is a protein expressed on leukocytes. LFA1 is a protein that interacts with intracellular adhesion molecule-1 (ICAM1) expressed by other tissues to slow circulating leukocytes, increasing leukocyte-tissue interactions, signaling, and activity.

Thus, the present invention relates to a method for diagnosing a disease state or condition, including an infection in a patient comprising administering to said patient an effective amount of a compound as generally described hereinabove to a patient suspected of or being at risk for having a disease state and/or condition as otherwise described herein and then diagnosing the existence of a disease or condition in said patient by imaging said patient and determining the existence of an imaging (radioimage) signal from tissue in said patient consistent with the existence of a disease state or condition. The method comprises comparing the image(s) obtained from the patient to one or more standard images (e.g. a standard for normal tissue and/or of diseased tissue of the patient or a population of patients to establish a standard). A determination that tissue or an organ in a patient is impact by a disease state and/or condition or infected and the extent and/or severity of infection is made by comparing the image from the tissue or organ suspected of being infected with the standard image. If the image from the tissue is significantly higher than a standard image from non-infected tissue, then a diagnosis that the tissue is infected may be made. Alternatively, if the image from the tissue is approximately the same as a standard image from infected tissue, then a diagnosis that the tissue is infected and the severity of infection may be made.

A particularly preferred group of compounds for use in the present invention are compounds according to the chemical structure:

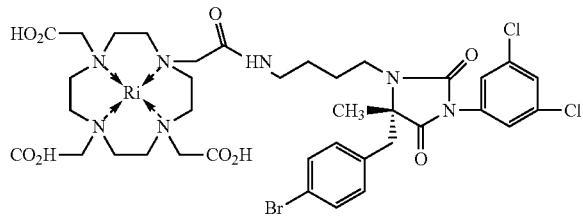

Where Ri is a radioisotope as otherwise described herein, more preferably $^{213}$Bi, $^{177}$Lu, $^{68}$Ga or $^{111}$In, including pharmaceutically acceptable salts thereof. The above compound may also be represented by the following chemical structure, where the carboxylate anions are complexed with the radionuclide.

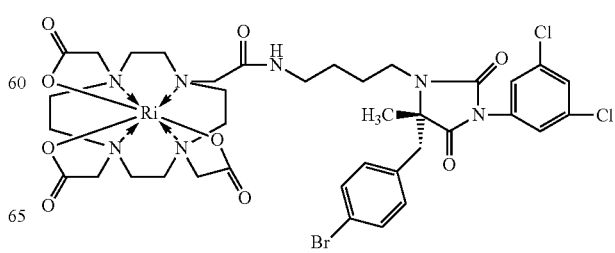

Where Ri is a radioisotope as otherwise described hereinbelow and more preferably $^{213}$Bi, $^{177}$Lu, $^{68}$Ga or $^{111}$In, including pharmaceutically acceptable salts thereof.

In particularly preferred aspects, Ri are $^{68}$Ga or $^{111}$In according to the following chemical structure (or a pharmaceutically acceptable salt/ion):

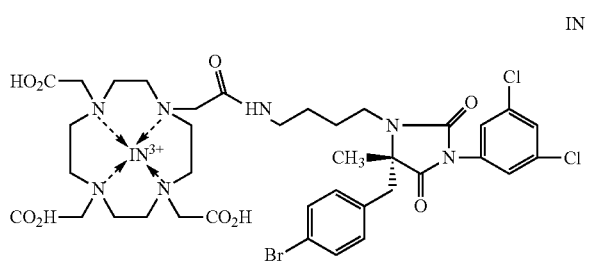

IN

Which may also be represented by the following structure:

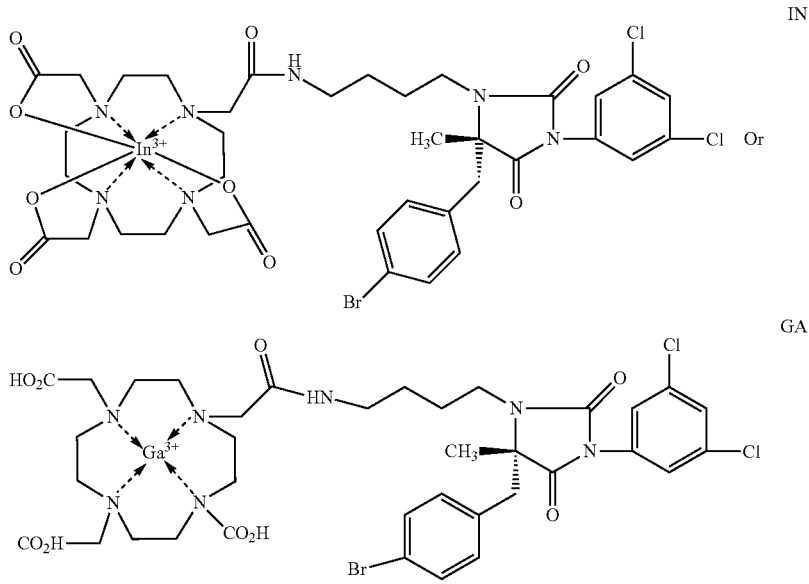

IN

GA

Which may also be represented by the following structure:

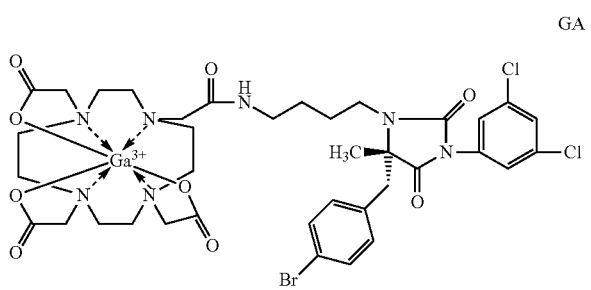

GA

It is noted that compounds according to the present invention (and in particular, compound IN or GA, above) exhibit a favorable bioavailability to tissues which have are to be diagnosed for disease states and/conditions, thus providing a ready means by which the infection may be diagnosed and/or monitored for therapeutic success or failure. It is noteworthy that the compounds also cross the blood brain barrier in certain circumstances such as inflamed menningis and other instances, which cause or result in a leaky blood brain barrier. Such leaky menningis are common in menningitis, MS, traumatic brain injury, concussion, PTSD, etc, making diagnosis and monitoring of these disease states and/or conditions in the brain effective.

In alternative embodiments, administration of compounds according to the present invention assist in monitoring therapies for treating a disease state or condition, including an infection wherein during treatment of the disease state or infection, a compound according to the present invention may be administered to a patient such that infected tissue may be imaged/monitored and optionally/preferably compared to a standard image (from normal or uninfected tissue and/or impacted/infected tissue, as a standard) in order to determine the effect of therapy on the diseased tissue. The therapy may thereafter be terminated because a cure has been effected, the same therapy may be continued to further treat the disease state, condition and/or infection, or the therapy may be modified in order to further treat the infection.

Disease states and/or conditions which are diagnosed and/or monitored according to the present invention include atherosclerosis, including atherosclerotic plaque in tissues, especially blood vessels, including often arteries and/or arterioles and including heart, aortic arch, descending aorta, carotids, femoral, profunda femoris, renal, hypogastric, iliac (common, interior and exterior), popliteal fossa, peroneal, anterior tibial artery, posterior tibial artery, anterior dorsalis pedis, abdominal aorta, celiac artery, gastric artery, hepatic artery, splenic artery, subclavian artery, axillary artery, brachial artery, radial artery, ulnar artery, thoracic aorta, superior mesenteric artery and inferior mesenteric artery of a patient, atherothrombosis in one or more of the same tissues, cerebral vascular disease, cerebral ischemia, cerebral infarct and meningitis as well as pneumonitis, pericarditis, multiple sclerosis, lupus erythematosus and pancreatitis.

BRIEF DESCRIPTION OF THE FIGURES

FIG. 1 shows the use of $^{111}$In-DANBIRT as an in vivo SPECT/CT imaging tool for the expression of LFA-1 in the inflammatory process of atheroma development.

FIG. 13 shows Table 1, direct to the [111In] In-DANBIRT animal study design. According to the study, ApoE$^{-/-}$ mice were exposed for 8 weeks to either normal chow or high fat chow for experiment samples.

FIG. 14 shows Table 2, which is directed to the UPLC method gradient with flow rate.

FIG. 15 shows Table 3, which shows the SPECT/CT imaging parameters using in the experiment.

DETAILED DESCRIPTION OF THE INVENTION

Figure 1A:
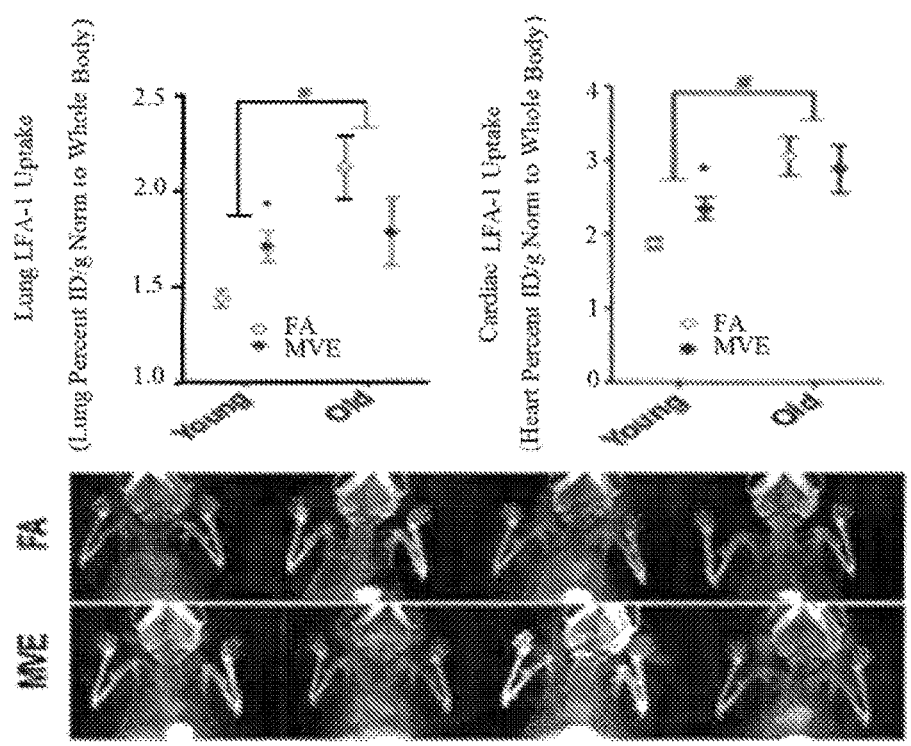
FIG. 1A shows the results of MVE induced cardiopulmonary inflammation in both lung and cardiac tissue.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "patient" or "subject" is used throughout the specification to describe an animal, preferably a human, to whom diagnosis or monitoring of treatment with the compounds according to the present invention is provided. For diagnosis, and monitoring treatment of those disease states and or conditions which are specific for a specific animal such as a human patient, the term patient refers to that specific animal. In addition to humans, domesticated animals are often patients and subjects according to the present invention.

The term "compound" is used herein to refer to any specific chemical compound disclosed herein. Within its use in context, the term generally refers to a single compound but in certain instances may also refer to stereoisomers and/or optical isomers (including racemic mixtures) of disclosed compounds, including pharmaceutically acceptable salts, solvates and polymorphs thereof.

The term "optionally substituted" shall mean a substituent other than H on a molecule of a compound, the substituent being compatible with the chemistry of the present invention. Substituents include $C_1$-$C_6$ alkyl groups (preferably, $C_1$-$C_3$ alkyl groups, which may be optionally substituted with for example, one or more halogen group, especially fluorine), halogen (F, Cl, Br or I), amine groups (which may be optionally substituted with one or two $C_1$-$C_3$ alkyl groups), O($C_1$-$C_6$)alkyl (alkoxy), OC(O)($C_1$-$C_6$)alkyl (ester), (O)CO($C_1$-$C_6$)alkyl (ester), $C_1$-$C_6$ amide or $C_1$-$C_6$ carboxamide (where the amine is unsubstituted, or mono- or di-$C_1$-$C_3$ alkyl substituted), among others.

The term "effective amount" is used throughout the specification to describe concentrations or amounts of compounds according to the present invention which may be used to diagnose a disease slate or monitor prognosis of a disease state, produce a favorable change in a disease or condition treated, whether that change is a remission, a favorable physiological result, a reversal or attenuation of a disease state or condition treated, the diagnosis, prevention or the reduction in the likelihood of a condition or disease-state occurring, depending upon the disease or condition treated. Where compounds are used in combination, each of the compounds is used in an effective amount, wherein an effective amount may include a synergistic amount.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from less than about 6 µSv (0.006 mSv) to 37 mSv or more. For reference, a common bone scan with 600 MBq of technetium-99m-MDP has an effective dose of about 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "ICAM-1/LFA-1 mediated disease" is used throughout the specification to describe a disease which is mediated through, occurs as a consequence of the interaction of ICAM-1 with LFA-1, for example, by inhibiting the ICAM-1/LFA-1 dependent homotypic aggregation of human lymphocytes and human lymphocyte adherence to ICAM-1, or modulating immune cell activation/proliferation, for example, as competitive inhibitors of intercellular ligand/receptor binding reactions involving CAMS and leukointegrins. These disease states include numerous disease states and conditions, especially atherosclerosis, atherothrombosis, cerebral vascular disease, cerebral ischemia, cerebral infarct and meningitis as well as pneumonitis, pericarditis, multiple sclerosis, lupus erythematosus and pancreatitis, as otherwise described herein. These disease states or conditions often produce levels of LFA-1 or ICAM receptors which are elevated as a consequence of disease state or condition and provide a target or approach for diagnosing, monitoring the treatment of and/or treating these diseases. It is noted that in certain conditions of the brain, it has been found that the blood brain barrier allows the compounds of the present invention to cross into the brain, thus facilitating diagnosis and/or monitoring of these disease states, which include cerebral vascular disease, cerebral ischemia, cerebral infarct and meningitis.

The present compounds and compositions may be used to treat varied disease states and conditions such as atherosclerosis, atherothrombosis, cerebral vascular disease, cerebral ischemia, cerebral infarct and meningitis as well as pneumonitis, pericarditis, multiple sclerosis, lupus erythematosus and pancreatitis. In this method one or more compounds according to the present invention, alone or in combination with at least one additional bioactive is administered to the patient or subject in need with one or more of the above-described disease states and/or conditions in order to inhibit, reduce or resolve the disease state and/or condition or reduce the likelihood that a disease state and/or condition will worsen or spread to other tissue.

In certain preferred aspects of the invention, compounds according to the present invention, and in particular, a compound according to the chemical structure;

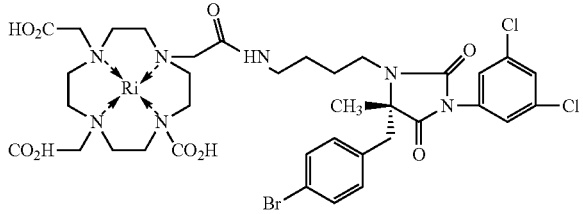

Also represented as:

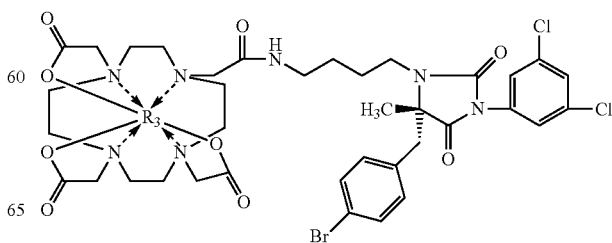

Where Ri is a radioisotope selected based on the physical half life, the decay mode (alpha, beta, auger, gamma, X-ray) and the energy of the radioisotope. Exemplary radioisotopes for use in the present invention include, for example, $^{86}$Y, $^{90}$Y, $^{111}$In, $^{177}$Lu, $^{225}$Ac, $^{209}$Bi, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{11}$As, $^{65}$Zn, $^{76}$Br, $^{48}$V, $^{49}$V, $^{89}$Zr, $^{203}$Pb, $^{209}$Pb, $^{212}$Pb, $^{166}$Ho, $^{153}$Pm, $^{201}$Tl, $^{188}$Re, $^{186}$Re, $^{99m}$Tc. In certain aspects of the present invention, preferred radioisotopes include, for example, $^{212}$Bi, $^{213}$Bi, $^{212}$Pb, $^{177}$Lu, $^{225}$Ac, $^{68}$Ga, $^{67}$Ga, $^{66}$Ga, $^{86}$Y, $^{90}$Y, or $^{111}$In, more preferably $^{213}$Bi, $^{177}$Lu, $^{111}$In, $^{68}$Ga, even more often, $^{68}$Ga and $^{111}$In, among others. $^{111}$In and $^{68}$Ga are preferred In certain preferred compounds Ri is a radioisotope (as a cation) as otherwise described hereinbelow, more preferably $^{213}$Bi (for example, as $^{213}$Br$^{3+}$), $^{177}$Lu (for example, as $^{177}$Lu$^{3+}$), $^{68}$Ga or $^{111}$In (for example, as $^{68}$Ga 3+ or $^{111}$In3+) are preferred. In particularly preferred aspects, Ri are $^{68}$Ga or $^{111}$In according to the following chemical structures:

IN

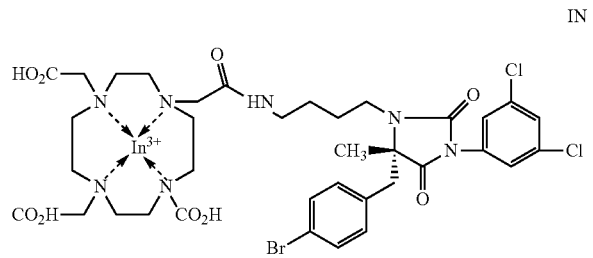

Which may also be represented as follows:

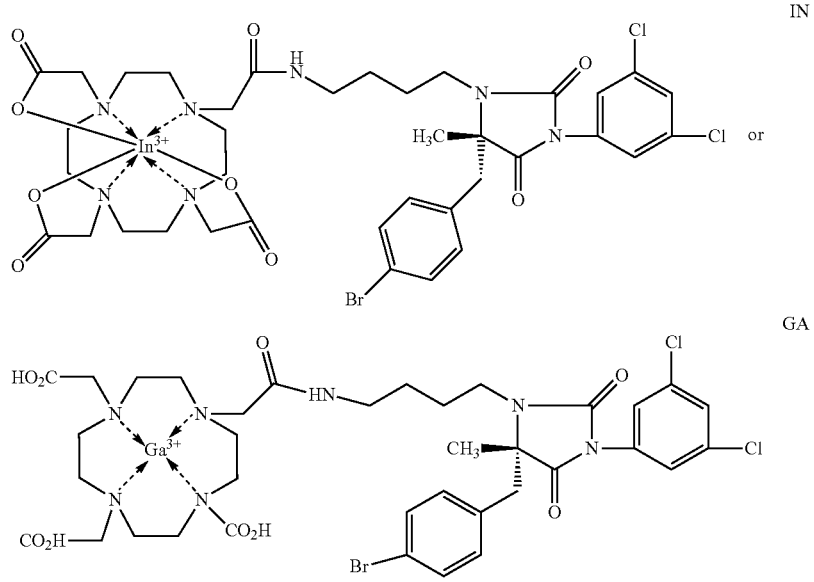

IN or

GA

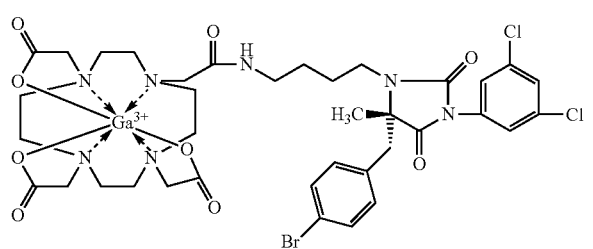

Which also may be represented as follows:

GA or a pharmaceutically acceptable salt, enantiomer, solvate or polymorph thereof.

The term "disease or condition" is used throughout the specification to describe clinically evident disease resulting from the presence, introduction or invasion of leukocytes and/or lymphocytes into a tissue characterized by a disease state and/or condition to be diagnosed, monitored, monitored and treated and/or treated according to the method of the present invention.

The terms "treat", "treating", and "treatment", etc., as used herein within context, also refers to any action providing a benefit to a patient at risk for any of the disease states or conditions which can be diagnosed, monitored and/or treated pursuant to the present invention. Disease states or conditions which may be diagnosed or treated by the present invention include, for example, atherosclerosis, especially atherosclerotic plaque in tissues, especially blood vessels, including often arteries and/or arterioles and including heart, aortic arch, descending aorta and carotids of a patient, atherothrombosis which may occur in those same tissues, diseases of the brain such as cerebral vascular disease, cerebral ischemia, cerebral infarct and meningitis as well as pneumonitis, pericarditis, multiple sclerosis, lupus erythematosus and pancreatitis. Treatment, as used herein, principally encompasses therapeutic treatment, but may also encompass both prophylactic and therapeutic treatment, depending on the context of the treatment. The term "prophylactic" when used, means to reduce the likelihood of an occurrence or the severity of an occurrence within the context of the treatment of a disease state or condition otherwise described herein.

The term "leukocytes" refers to white blood cells in a patient's blood. The cellular components of blood include erythrocytes (red blood cells), leukocytes (white blood cells), and platelets. Normal human blood contains between about 4000-10,000 leukocytes/µl. Leukocytes are divided into five classes based on morphological and tinctorial characteristics when stained. The five classes of leukocytes are:
neutrophils (40%-75%);
eosinophils (1%-6%);
basophils (less than 1%);
monocytes (2%-10%), and
lymphocytes (20%-45%)

For purposes of the present invention, monocytes and lymphocytes are important cellular components of leukocytes. Monocytes, when recruited to tissues, become macrophages. Macrophages may occur when a monocyte enters damaged tissue through the endothelium of a blood vessel, a process known as leukocyte extravasation. There, the moncyte undergoes a series of changes to become a macrophage Monocytes are attracted to a damaged site by chemical substances through chemotaxis, triggered by a range of stimuli including damaged cells, pathogens and cytokines released by macrophages already at the site. Unlike short-lived neutrophils, macrophages survive longer in the body up to a maximum of several months.

Macrophages are the predominant cells involved in creating the progressive plaque lesions of atherosclerosis. Focal recruitment of macrophages occurs after the onset of acute myocardial infarcation and in other instances. These macrophages function to remove debris, apoptotic cells and to prepare for tissue regeneration.

Collectively, neutrophils, eosinophils, and basophils are known as granulocytes due to the presence of granules in their cytoplasm. In addition, monocytes and lymphocytes are also known as mononuclear cells.

The term "Lymphocytes" refers to a subset of white blood cells or leukocytes. Lymphocytes represent about 20% to about 45%. A lymphocyte is a type of white blood cells that is part of the immune system. Two main types of lymphocytes are B-cells and T-cells. B-cells are characterized by the presence of immunoglobulins on their surface, and upon stimulation with antigen, they are transformed into plasma cells. Plasma cells are then able to secrete antibodies specific to the antigen. T-cells take part in cell mediated immune response, which does not depend on the presence of circulating antibodies. T cells destroy the body's own cells that have themselves been taken over by viruses or become cancerous. Lymphocyte number are relevant to diagnosis of cancer and may be upregulated (increased compared to normal) or downregulated (reduced compared to normal) depending upon the type of cancer or the stage of cancer which is diagnosed. Early stage cancer tends to have higher lymphocyte numbers compared to later stage cancers, which show reduced lymphocyte activity.

The term "pharmaceutically acceptable" refers to a salt form of the present compounds (an acid or base addition salt, among others well known in the art) or a carrier, additive or excipient which is not unacceptably toxic to the subject to which it is administered. Compounds according to the present invention include pharmaceutically acceptable salt forms where applicable.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases and conditions as otherwise described herein. This technique also contributes to improving the treatment of these disorders by optimizing the pre-clinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, melanoma and metastatic melanoma according to the present invention.

There are a number of different imaging modalities that can be used for noninvasive molecular imaging, using compounds according to the present invention. Each has different strengths and weaknesses and some are more adept at imaging multiple targets or sites than others. This is important in instances where atherosclerosis or other disease state is suspected. The modalities which can be used in the present invention are varied and in the present invention principally include single photon emission computed tomography (SPECT), SPECT/CT which combined SPECT imaging with computer tomography (CT), and positron emission tomography (PET), discussed below.

The main purpose of SPECT when used in melanoma imaging pursuant to the present invention is to measure the distribution of radioisotope in skin tissue, in particular, those skin regions and other tissues where melanoma, including metastatic melanoma, is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}$Tc, $^{111}$In, $^{123}$I, $^{201}$Tl, $^{67}$Ga, $^{99m}$Tc and $^{203}$Pb, among other gamma ray emitters) that can be used in the present invention and imaged with SPECT technology. In SPECT, where possible, by rotating the gamma camera around the area to be analysed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution.

Another imaging technique which finds particular use in the present invention is positron emission tomography (PET). In PET, a molecule is tagged with a positron emitting isotope. These positrons (β particles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, among others, including the preferred $^{66}$Ga, $^{68}$Ga, $^{64}$Cu, $^{86}$Y. One of the major disadvantages of PET is that most of the radioisotopes must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity; a typical PET scanner can detect between $10^{-11}$ mol/L to $10^{-12}$ mol/L concentrations.

The present compounds, compositions and methods are readily adaptable to conventional nuclear medicine techniques to provide diagnostic, monitoring and therapeutic approaches pursuant to the present invention.

The term "standard" is used to describe a set or reference measurement(s) made with for example, normal or non-diseased tissue (or, in some cases diseased and non-treated tissue) such that a comparison with a tested sample or samples can be made to determine the existence or absence of a disease-state or condition in the tested sample (which is usually in the patient's body) or the effectiveness of a therapeutic treatment. In the present invention, standards may be determined by taking measurements using normal tissue and/or the absence of a condition or disease state or a measurement, among other methods, for which the diagnostic assay is used. Standards are well known in the an and are determined using well known methods available in the art. Standards may vary from application to application depending upon the diagnostic method utilized. Standards may be developed from a single patient (including the patient to be diagnosed and/or or treated) or from a population of normal patients and/or patients with a disease state or condition to be diagnosed or monitored.

The term "coadministration" or "combination therapy" is used to describe a diagnosis, monitoring of therapy or treatment of a disease state and/or condition in which at least two active compounds (one of which is a compound according to the present invention) in effective amounts are used to treat a disease state and/or condition otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more bioactive agent which are useful in the treatment of the disease state or condition for which a patient is being diagnosed and/or monitored for the effectiveness of therapy.

The term "bioactive agent" is used to describe an agent such as a small molecule, a drug or other molecular entity which provides a particularly pharmacological or therapeutic effect. The bioactive agent may be any agent which treats one or more of the disease states and/or conditions which may be diagnosed, monitored and/or treated pursuant to the present invention including atherosclerosis, especially atherosclerotic plaque in tissues, especially blood vessels, including often arteries and/or arterioles and including heart, aortic arch, descending aorta and carotids of a patient, atherothrombosis which may occur in those same tissues, diseases of the brain such as cerebral vascular disease, cerebral ischemia, cerebral infarct and meningitis as well as pneumonitis, pericarditis, multiple sclerosis, lupus erythematosus and pancreatitis.

Preparation of compounds according to the present invention proceeds using standard synthetic chemical techniques which are readily available in the art. Synthetic methods for obtaining compounds related to the present invention may be found in U.S. Pat. No. 6,881,747, issued Apr. 19, 2005, which is incorporated by reference herein. These methods can serve as guides for obtaining compounds according to the present invention. In general, the present compounds may be made by condensing a chelate compound to which is bound a radionuclide onto an activated moiety containing either an electrophilic group or a nucleophilic group of a linker group which is chemically linked to the amine of the dioxoimidazolidine group of the compounds according to the present invention. Alternatively, the chelate may be first reacted with one end of a difunctional chemical linker and the unreacted moiety of the linker group may thereafter be reacted with the dioxoimidazoline group. Radioisotopes may be added (chelated) to the compound at an early or later stage in the chemical synthetic method. The chemical synthetic approaches for producing compounds according to the present invention is well known in the art.

As discussed above, tricarbonyl complexes may be used to prepare the final diagnostic/therapeutic compound according to the present invention. Preparation of the compound can also be prepared using Technetium (I) and Rhenium (I) tricarbonyl complexes such as those listed below using methods described by H.-J. Pietzsch, A. Gupta, M. Reisgys, A. Drews, S. Seifert, S. Seifert, et. al. [Chemical and Biological Characterization of Technetium(I) and Rhenium(I) Tricarbonyl Complexes with Dithioether Ligands Serving as Linkers for Coupling the Tc(CO)$_3$ and Re(CO)$_3$ Moieties to Biologically Active Molecules, *Bioconjugate Chem.*, 11(3) 414-424, 2000].

Bromo(3,6-dithiaoctane-S,S)tricarbonylrhenium(I)]

[Bromo(4,7-dithia-1-octyne-S,S)tricarbonylrhenium(I)]

[Bromo(1-carboxy-3,6-dithiaheptane-S,S)tricarbonylrhenium(I)] ($C_9H_{12}BrO_5ReS_2$)

[Bromo(1,6-dicarboxy-2,5-dithiahexane-S,S)tricarbonylrhenium(I)] ($C_9H_{10}BrO_7ReS_2$)

[1-Carboxylato-3,6-dithiaheptane-O,S,S)tricarbonylrhenium(I) ($C_9H_{11}O_5ReS_2$)

[(1-Carboxylato-6-carboxy-2,5-dithiahexane-O,S,S)tricarbonylrhenium(I)] ($C_9H_9O_7ReS_2$)

[Bromo(1,8-dihydroxy-3,6-dithiaoctane-S,S)tricarbonylrhenium(I)] ($C_9H_{14}BrO_5ReS_2$)

[(1,8-Dihydroxy-3,6-dithiaoctane-O,S,S)tricarbonylrhenium(I)]nitrate ($C_9H_{14}NO_8ReS_2$)

[Chloro(3,6-dithiaoctane-S,S)tricarbonyltechnetium(I)]

[Chloro(4,7-dithia-1-octyne-S,S)tricarbonyltechnetium (I)]

[Chloro(1-carboxy-3,6-dithiaheptane-S,S)tricarbonyltechnetium(I)]

[Chloro(1,6-dicarboxy-2,5-dithiahexane-S,S)tricarbonyltechnetium(I)]

[1-Carboxylato-3,6-dithiaheptane-O,S,S)tricarbonyltechnetium(I)

[(1-Carboxylato-6-carboxy-2,5-dithiahexane-O,S,S)tricarbonyltechnetium(I)]

The tricarbonyl complexes as described above may be reacted with the dioxoimidazoinyl compound to form a chemically linked tricarbonyl complex which contains the radioisotope.

Attachment of metal radioisotopes to the compounds prepared above make the final diagnostic/therapeutic compounds, especially Danbirt compounds. Analogous preparations yield compounds containing other radioisotopes as otherwise disclosed herein.

Linkers:

The linkers are comprised of alkyl chains of various lengths and containing various side chains (optionally substituted) depending on the hydrophobic/hydrophilic properties of the final product and the clinical needs. Linkers preferably contain O, S or NH or other functional group on the distal end of the molecule in order to attach a chelate to which may be bound a radioisotope. Simple condensation or other reactions may be used to covalently link the linker to the chelate so that a radionuclide may be complexed accordingly.

Chelates:

Are selected based on the metal/radioisotope to be incorporated and the clinical objectives (diagnosis and/or monitoring).

Chelates selected is such as those listed above and include

Open-Chain

Polyaminocarboxylates; AZA Macrocyclics; Polyaminocarboxylic Macrocycles; and

Polyaminophosphonate Macrocycles.

Chelates for inclusion in the present application are selected based on the metal to be incorporated and the clinical objectives. Chelates selected for use in the present invention include those listed below. Representative chelates are presented hereinabove and are otherwise disclosed and/or described in Brechbiel, *O J. Nucl. Med. Mol. Imaging,* 52(2) pp. 166-173 (June, 2008), which is incorporated by reference herein.

Open-Chain Polyaminocarboxylates:
    edta: ethylenediaminetetraacetic acid
    dtpa: diethylenetriaminepentaacetate
    ca-dtpa
    ibca-dtpa
    1B4M-dtpa
    lys-dtpa
    CHX-A" dtpa
    Vinyl dtpa
    Glu-dtpa AZA Macrocyclics
    cyclen: 1,4,7,10-tetraazacyclododecane
    cyclam: 1,4,8,11-tetraazacyclotetradecane
    bridged-cyclam: 1,4,8,11-tetraazabicyclo[6.6.2]hexadecane
    et-cyclam: 1,4-ethano-1,4,8,11-tetraazacyclotetradecane
    cylamdione: 3,9-dioxy-1,4,8,11-tetraazacyclotetradecane
    diamsar: 1,8-diamino-3,6,10,13,16,19-hexaazabicyclo(6,6,6)eicosane Polyaminocarboxylic Macrocycles
    dota: 1,4,7,10-tetraazacyclododecane-1,4,7,10-tetraacetic acid
    trita: 1,4,7,10-tetraazacyclotridecane-1,4,7,10-tetraacetic acid
    teta: triethylenetetramine bridged-cyclam-2a: 1,4,8,11-tetraazabicyclo[6.6.2]hexadecane-1,8-di(methanephosphonic acid)
    do3a: 1,4,7-tris(carboxymethyl)-1,4,7,10-tetraazacyclododecane
    do2a: 1,4,7,10-tetraazacyclododecane-1,7-bis(acetic acid)
    C-DOTA
    PA-DOTA
    DODASA
    Lys-DOTA
    C-NOTA
    N-NOTA
    NODASA
    2C-TETA
    6C-TETA
    BF-PEPA
    BF-HEHA
    TCMC (contains amides rather than carboxylates on the chelating moiety)

Polyaminophosphonate Macrocycles
    dotp: 1,4,7,10-tetraazacyclododecane-1,4,7,10-tetra(methanephosphonic acid)
    do3p: 1,4,7,10-tetraazacyclododecane-1,4,7-tri(methanephosphonic acid)
    do2p: 1,4,7,10-tetraazacyclododecane-1,7-di(methanephosphonic acid)

In one embodiment, the present invention relates to a diagnostic aspect of the invention which comprises administering a compound according to the present invention to a patient or subject to determine the existence of a disease or condition where LFA-1 expression is elevated such as in a disease state or condition as otherwise described herein and through measuring the radioactive decay of the isotope through any method known in the art, as discussed above, determining the presence and/or state of the disease and/or condition and the state of the tissue in the patient or subject. The diagnostic method according to the present invention may facilitate therapy once diagnosis of cancer or other disease state or condition, especially including the infectious disease as otherwise described herein is made.

In an additional aspect of the present invention, the present compounds and compositions may be used to diagnose and/or monitor the treatment of disease and conditions which are mediated through a cellular response which is undesirable and/or which should be controlled or inhibited, especially including where LFA-1 expression is elevated. Such infectious disease states or conditions include atherosclerosis, atherothrombosis, cerebral vascular disease, cerebral ischemia, cerebral infarct and meningitis as well as pneumonitis, pericarditis, multiple sclerosis, lupus erythematosus and pancreatitis, etc. as disclosed herein.

Without being limited by way of theory, it is believed that the present compounds also may be used therapeutically either by virtue of the inhibitory or stimulatory activity of the compounds within the context of the therapy of the disease state or condition.

The present invention is also directed to pharmaceutical compositions comprising an effective amount of a compound according to the present invention, including the pharmaceutically acceptable acid or base addition salts of compounds of the present invention, optionally in combination with a pharmaceutically acceptable carrier, additive or excipient. These compounds may be used alone or in combination with other bioactive agents which are used to treat disease states and/conditions described herein, especially atherosclerosis, atherothrombosis, cerebral vascular disease, cerebral ischemia, cerebral infarct and meningitis as well as pneumonitis, pericarditis, multiple sclerosis, lupus erythematosus and pancreatitis as described herein.

While not being limited by way of theory, it is believed that the compounds of the present invention inhibit or otherwise modulate the ICAM-1/LFA-1 dependent homotrypic aggregation of human lymphocytes and human lymphocyte adherence to ICAM-1. While not being limited by way of theory, it is believe that these compounds also have therapeutic utility in the modulation of immune cell activation/proliferation, e.g., as competitive inhibitors or stimulators (because of the introduction of radiation) of intercellular ligand/receptor binding reactions involving CAMs and Leukointegrins. Thus the activity and therapeutic activity of compounds according to the present invention is broad-based.

Regardless of the mechanism, the compounds of the present invention may be used to diagnose, identify, monitor and/or treat conditions or disease states in patients or subjects who suffer from those conditions or disease states or are at risk for disease states or conditions from these disease states and/or conditions including atherosclerosis, atherothrombosis, cerebral vascular disease, cerebral ischemia, cerebral infarct and meningitis as well as pneumonitis, pericarditis, multiple sclerosis, lupus erythematosus and pancreatitis.

The amount of compound used in the present invention is that amount effective within the context of the administration. A suitable oral dosage for a compound according to the present invention may vary over a wide range, for example, within the range of about 0.001 µg to up to 1 mg or more for diagnostic applications, often about 0.01 µg to about 500 µg or about 0.1 µg to about 100 µg, and about 0.001 mg to 10 g or more per day, preferably about 0.01 mg to about 50 mg per day, more often 0.1 to about 10 mg per day for therapeutic applications. In parenteral formulations, a suitable dosage unit may contain from about 0.001 µg to 250 mg or more of said compounds depending on application, which may be administered from one to four times per day, whereas for topical administration, formulations containing 0.01 to 1% active ingredient are often used formulated to provide a dose range as above. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository. In certain instances, the compounds according to the present invention may be formulated in combination with other bioactive agents which are used to treat the disease states and/or conditions such as atherosclerosis, atherothrombosis, cerebral vascular disease, cerebral ischemia, cerebral infarct and meningitis as well as pneumonitis, pericarditis, multiple sclerosis, lupus erythematosus and pancreatitis in order to facilitate the monitoring of therapy associated with these disease states and/or conditions.

EXAMPLES

Examples and related figures evidencing methods associated with the present invention and efficacy of the claimed invention are presented herein.

Example 1

This first example is presented to show evidence of the use of the present invention in diagnosing the inflammatory process associated with atherosclerosis. In particular, in this example, $^{111}$In-DANBIRT is used as an in vivo SPECT/CT imaging tool for the Expression of LFA-1 in the inflammatory process of atheroma development.

The objective of this experiment was to assess inflammatory leukocyte presence and accumulation in vascular atherosclerotic plaque using $^{111}$In-DANBIRT as a non-invasive diagnostic imaging tool.

Methods: 6 week ApoE KG mice were fed either normal or high fat chow (n=8 per group) for 8 weeks to induce vascular atherosclerotic lesions. SPECT/CT imaging was performed 3-hrs post injection of ~700 uCi of $^{111}$In-DANBIRT at baseline, 4 weeks and 8 weeks. Whole body Autoradiography was performed 24-hrs post injection after 8-week time point. Image processing and analysis was performed by region of interest (ROI) determination in relationship to voxel and volume, uptake quantification was normalized to muscle uptake. Blood partition assays were conducted to ascertain specific binding components.

Figure 1B:
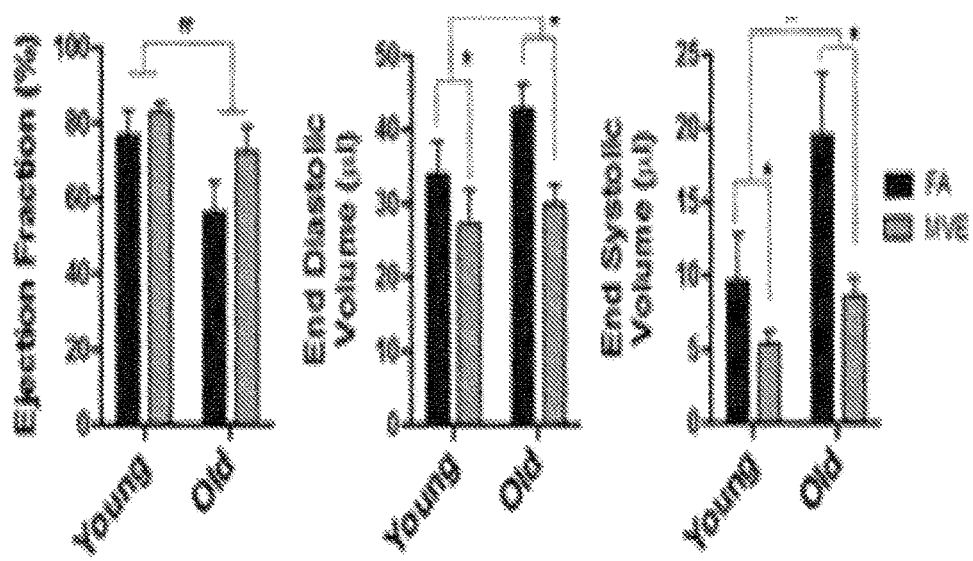
FIG. 1B shows the end diastolic/systolic volumes decreased by MVE.
Figure 2:
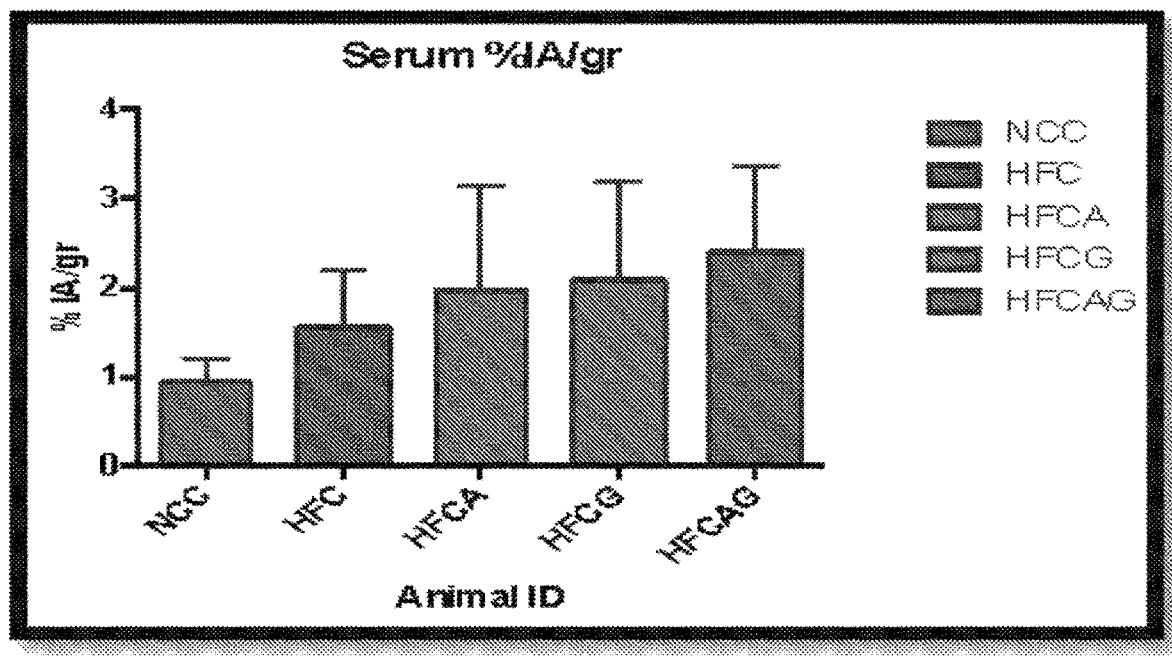
FIGS. 2-7 show the results of an organ bio distribution assay. These results evidenced significant uptake in the liver, serum, aorta and in different blood components (FIGS. 2-7). Radiolabeling was successful having a specific activity of 2.86 mCI/nmole that shows high incorporation yield (>98%) of $^{111}$In-DANBIRT.
Figure 3:
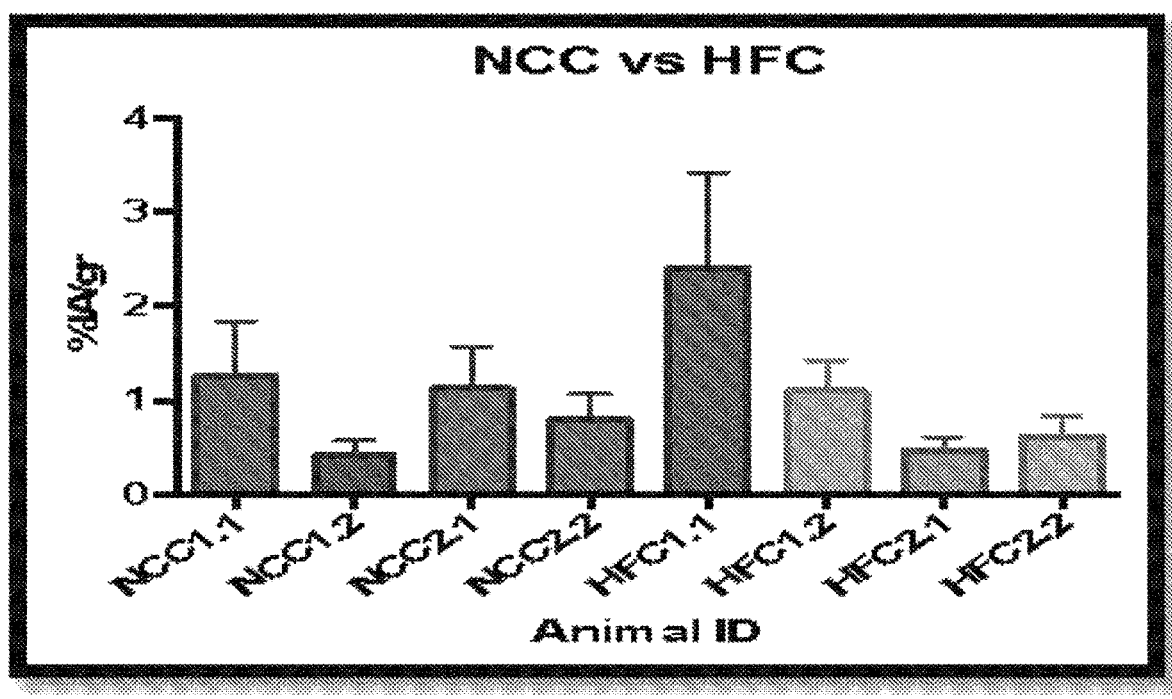
Figure 4:
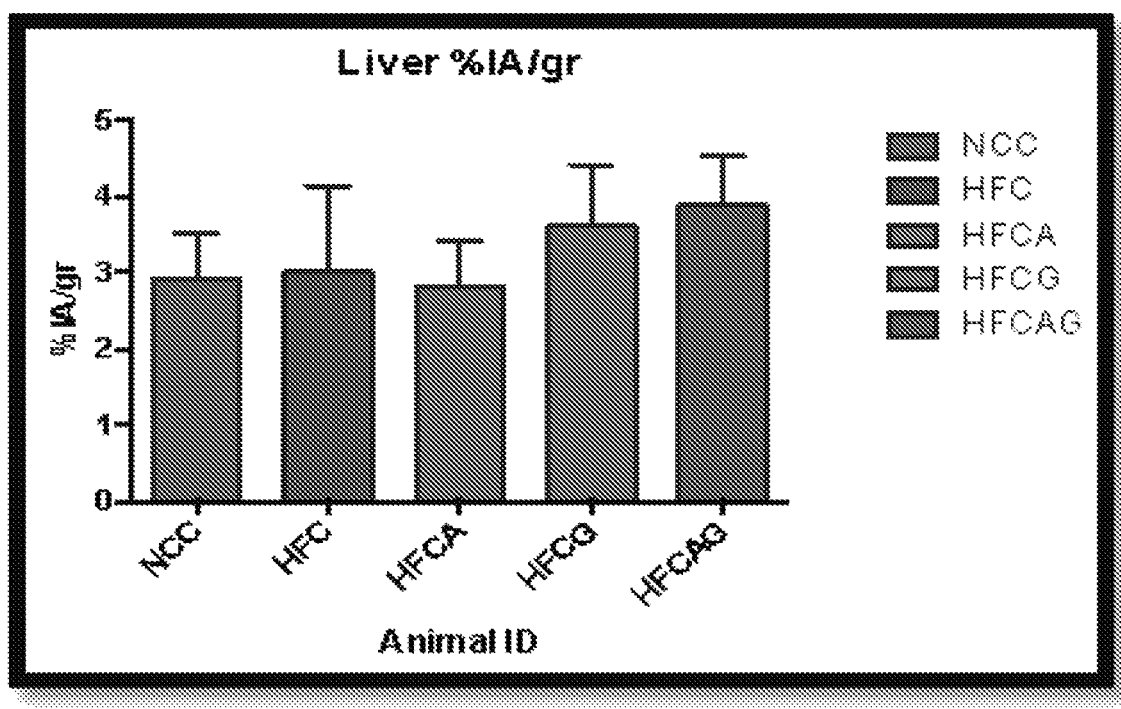
Figure 5:
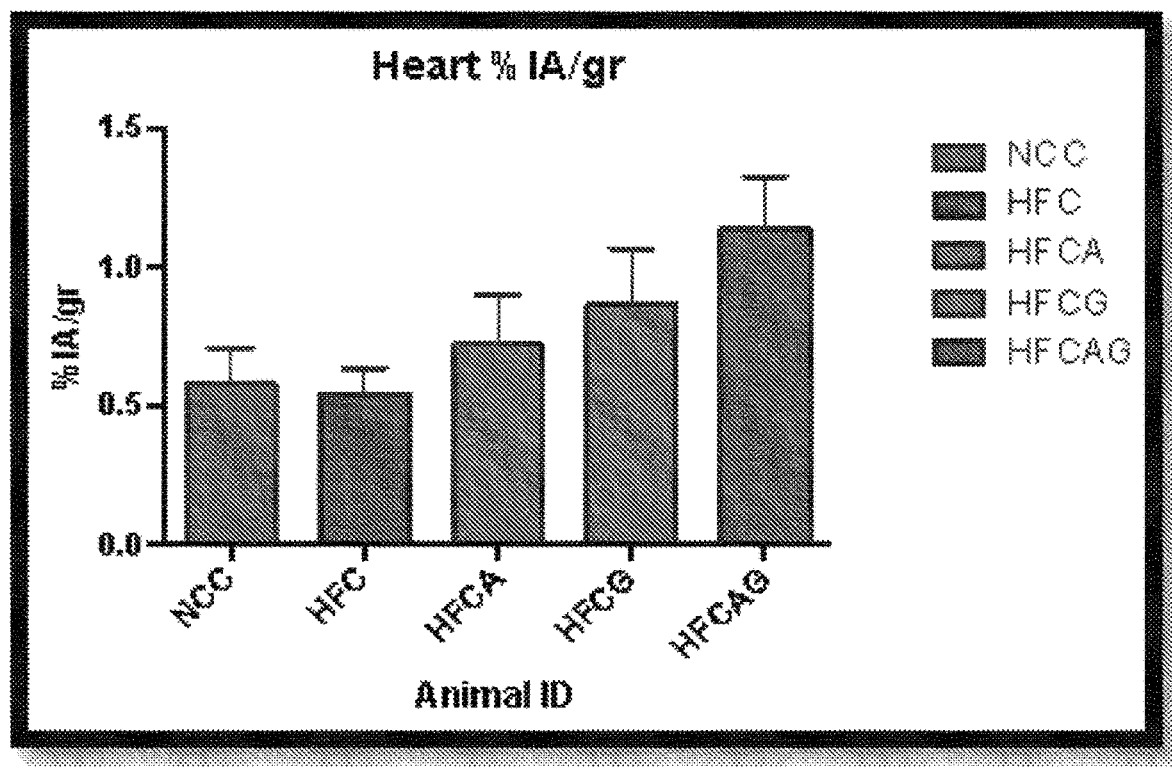
Figure 6:
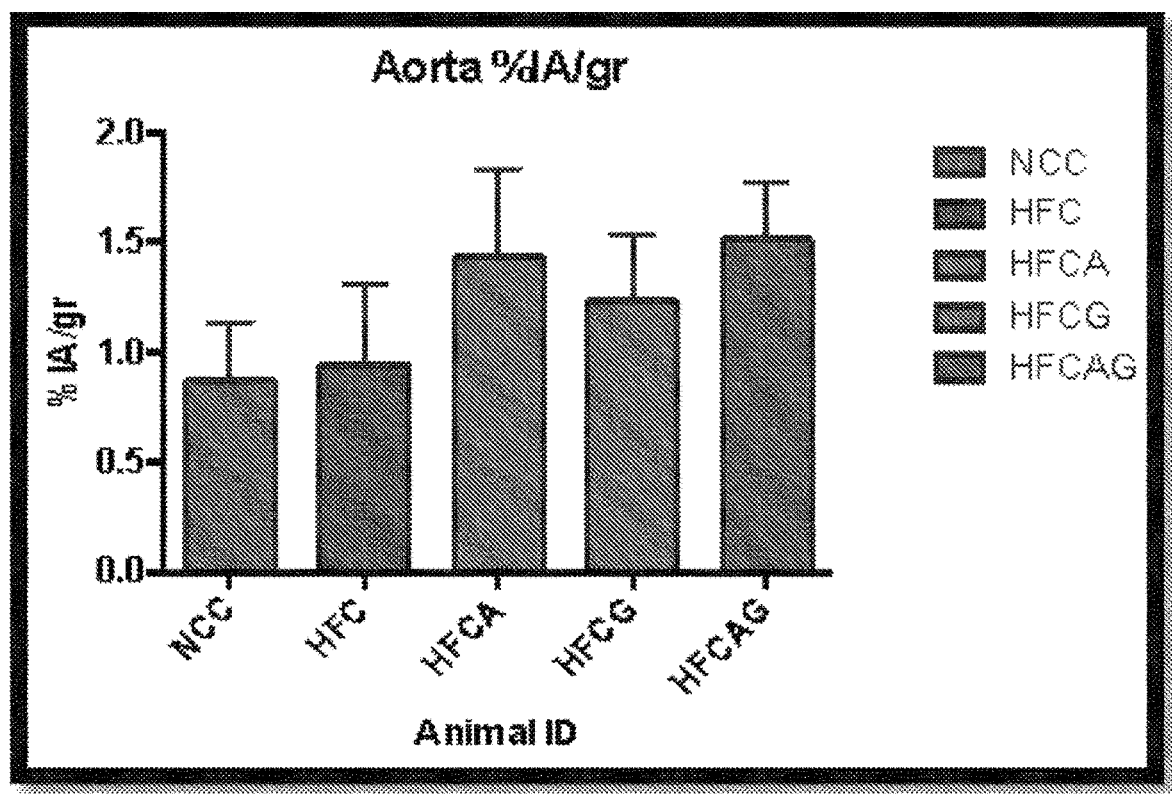
Figure 7:
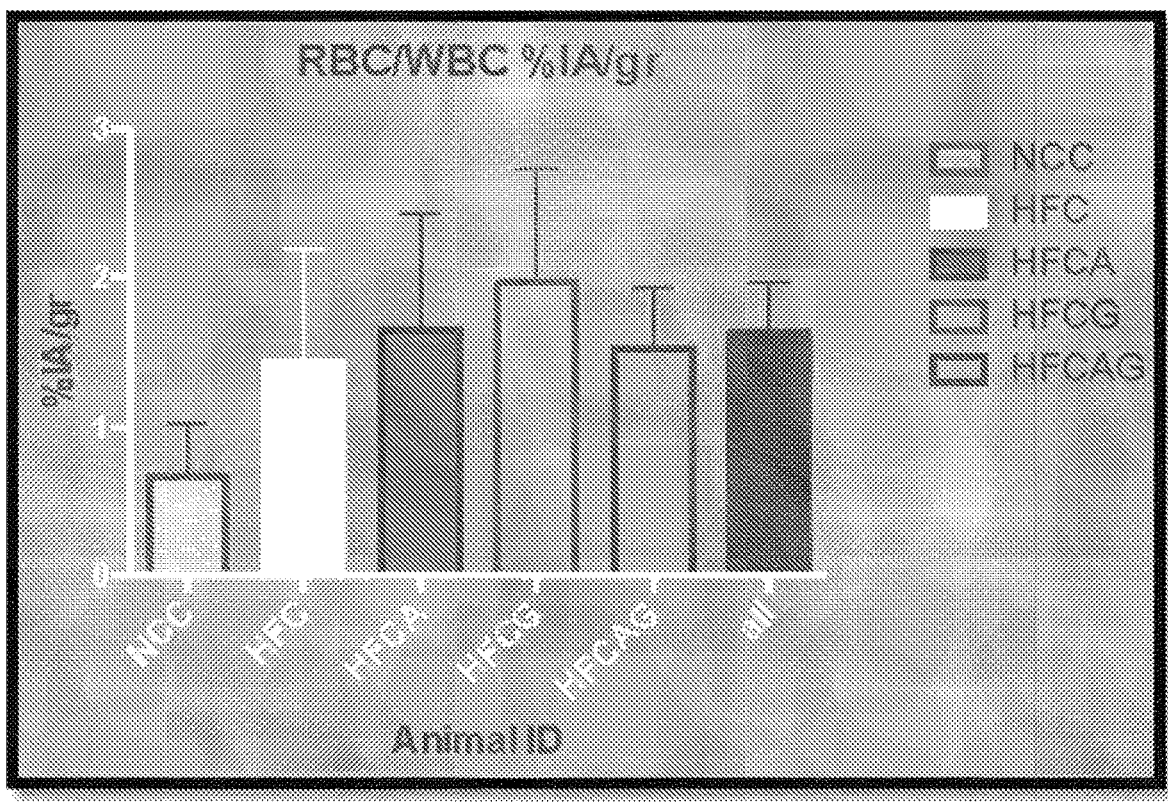

Results: autoradiography and SPECT/CT analysis characterized $^{111}$In-DANBIRT distribution in cardiovascular tissues (heart, aortic arch, descending aorta, carotids). A longitudinal increase in uptake was evidenced when comparing high fat diet to normal diet mice along our different time points. Increased uptake was evidenced in the thymus, which would be consistent with increased immune response to vascular injury. Whole blood isolation correlated these findings showing increased specific uptake by neutrophils in our ozone-exposed group. FIG. 1A shows the results of MVE induced cardiopulmonary inflammation in both lung and cardiac tissue. FIG. 1B shows the end diastolic/systolic volumves decreased by MVE.

Conclusion: this initial study showed that ApoE KO mice on Western diet exhibit increased cardiovascular and immune tissue uptake of $^{111}$In-DANBIRT compared to mice on a normal diet. Further studies to assess vascular lesion development in the disease model using biochemical markers and histology are to be undertaken. These findings support initial development toward a more advanced vascular disease model that will validate $^{111}$In-DANBIRT as a diagnostic tool for assessment of inflammation in cardiovascular injury models.

Example 2

The aim of this example is to validate $^{111}$In-DANBIRT as a non-invasive diagnostic tool using SPECT/CT imaging for inflammation assessment in vulnerable atherosclerotic plaque in a murine model.

Method for Example 2
 SPECT/CT images were obtained from 2 different cohorts over 3 identical imaging time points (0 weeks (baseline), 4 weeks and 8 weeks),
 6 week old ApoE KO C57 black male mice
 We focused on 3 specific areas in our SPECT/CT imaging analysis: Heart, aortic arch and descending aorta; normalized to muscle.

| 1st Cohort n = 40 | | | | | |
|---|---|---|---|---|---|
| | Normal Diet | High Fat Diet | High Fat Diet + Statin | High Fat Diet + GW501516 | High Fat Diet + Statin + GW501516 | Total |
| SPECT/CT and bio distribution | 4 | 4 | 4 | 4 | 4 | 20 |
| Serum analysis | 4 | 4 | 4 | 4 | 4 | 20 |
| Total | 8 | 8 | 8 | 8 | 8 | 40 |

Animals were imaged for ~75 minutes 3 hrs post tail vein injection of ~700 uCi (~25.9 Mbq) of $^{111}$In-DANBIRT
Atorvastatin was administered in the drinking water and PPAR-Delta agonist (GW1516) was incorporated into food pellets by diet manufacturing company.
Organ and serum collection for bio distribution and lipid levels and sub particles size analysis was performed after last imaging time point

| 2nd Cohort n = 8 | | |
|---|---|---|
| | Normal Diet | High Fat Diet | Total |
| SPECT/CT and Autoradiography | 4 | 4 | 8 |

6 week old ApoE KO C57 black male
SPECT imaging 3 hrs and 24 hrs post tail vein Injection of ~700 uCi (~25.9 Mbq) of $^{111}$In-DANBIRT
Autoradiography was performed 24 hrs PI of $^{111}$In-DANBIRT after the last imaging time point,
We focused on 3 areas for our region of interest analysis: Aortic arch, carotids and thymus: normalized to muscle.
Whole blood incubation with $^{68}$Ga-DANBIRT and subsequent neutrophil and PBMC isolation were performed from rat blood from animals exposed to filtered air and ozone.
2 groups: Filtered air (n=3) and ozone (n=3)
Whole blood was collected 24 hrs post exposure
Whole Blood Separation was performed after incubation with $^{68}$Ga-DANBIRT, obtaining 4 samples: serum, red blood cells, neutrophils and peripheral blood mononucleated cells. Staining was performed for specific morphology interpretation and smear cell line purity assessment.

Results

Organ bio distribution assay showed significant uptake in the liver, serum, aorta and in different blood components (FIGS. 2-7). Radiolabeling was successful having a specific activity of 2.86 mCI/nmole that shows high incorporation yield (>98%) of $^{111}$In-DANBIRT.

Figure 8:
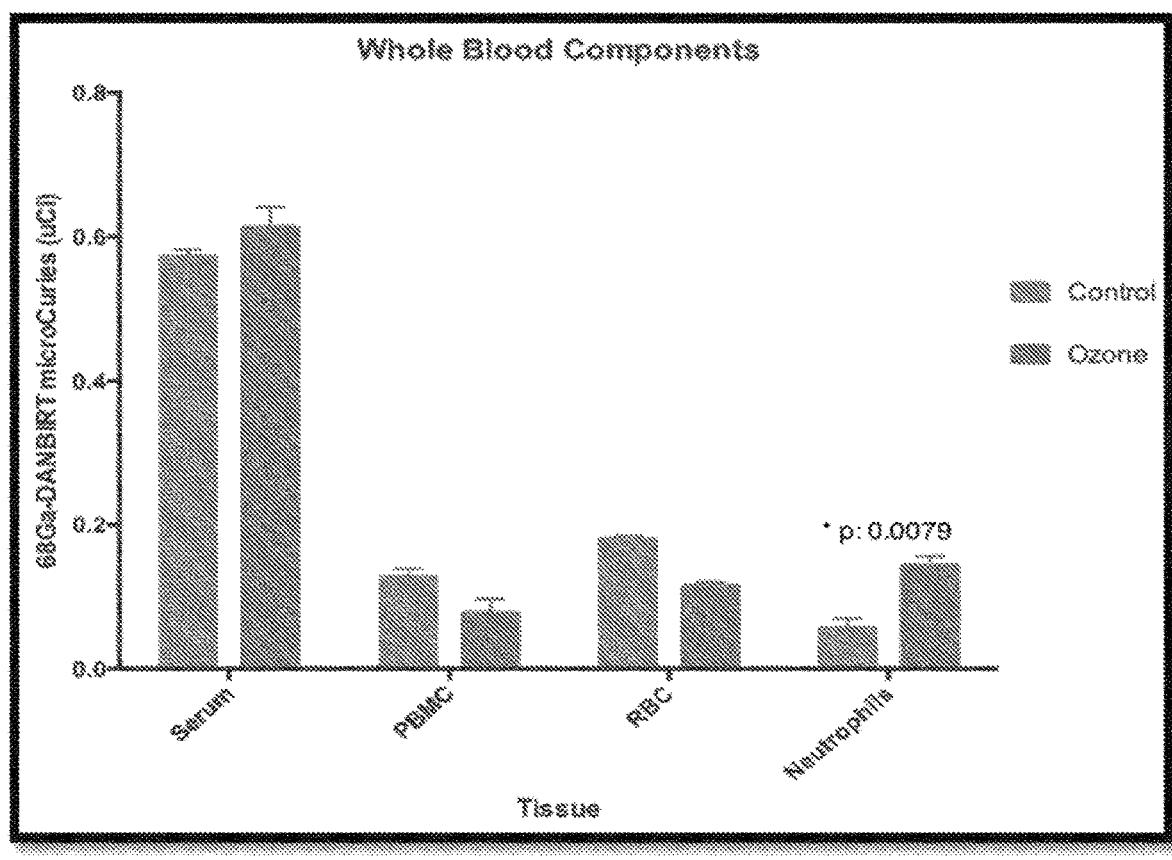
FIG. 8 shows the results of an in vitro assay to determine the ideal specific binding to leukocyte subpopulations (neutrophils and PBMCs). The results show an increase in uptake in ozone-exposed neutrophils, no significant results in the PBMC sample.

After the initial bio distribution results the inventor decided to follow up on the findings and illustrate in an in vitro assay the ideal specific binding to leukocyte subpopulations (neutrophils and PBMCs) under a model that has shown an adequate acute immune response on whole blood isolation methods (FIG. 8). This translated to an increase in uptake in ozone-exposed neutrophils, no significant results in our PBMC sample. See FIG. 8.

Figure 9A:
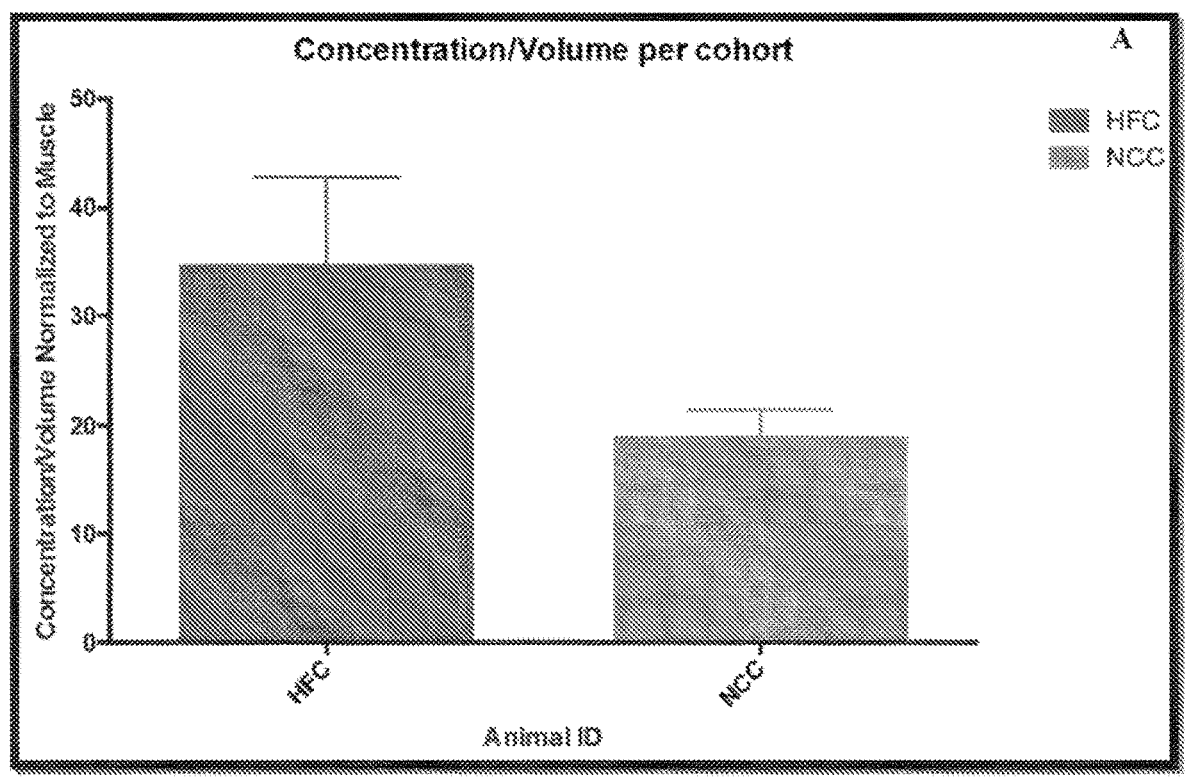
FIGS. 9A and B, 10A-C and 11 show the results of a 24 hour autoradiography assay (FIGS. 9 A and B and FIG. 11) and a 3 hour SPECT/CT (FIG. 10) analysis correlated the findings and gave a clear idea regarding the radioisotope distribution in cardiovascular tissue (heart, aortic arch, carotids). The results also showed increased uptake in the thymus, which is consistent with increased immune response to vascular injury.
Figure 9B:
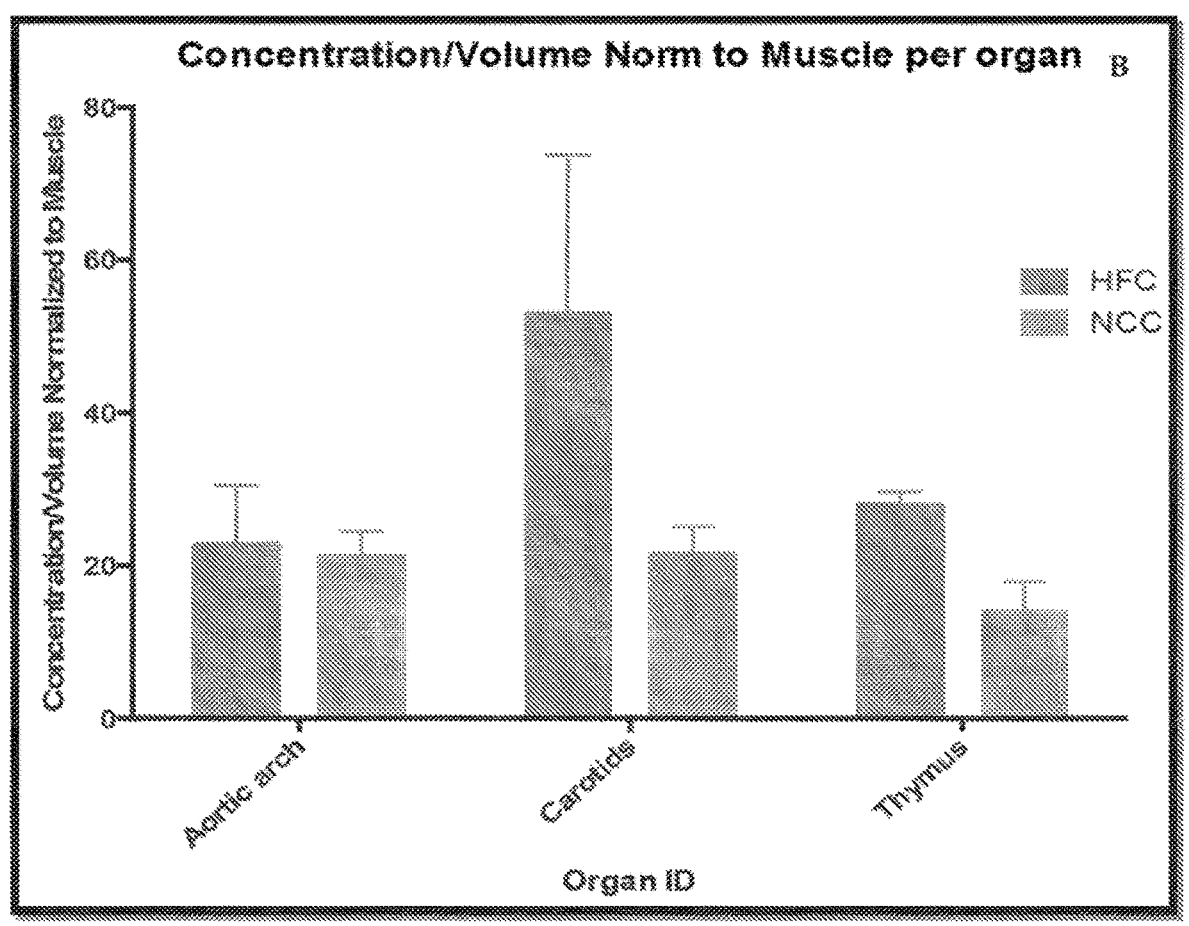
Figure 10A:
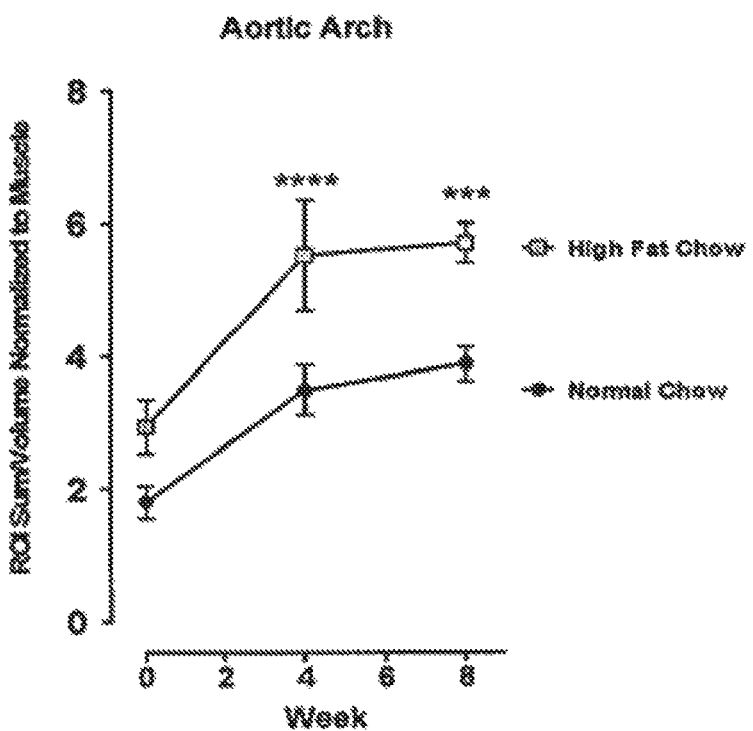
Figure 10B:
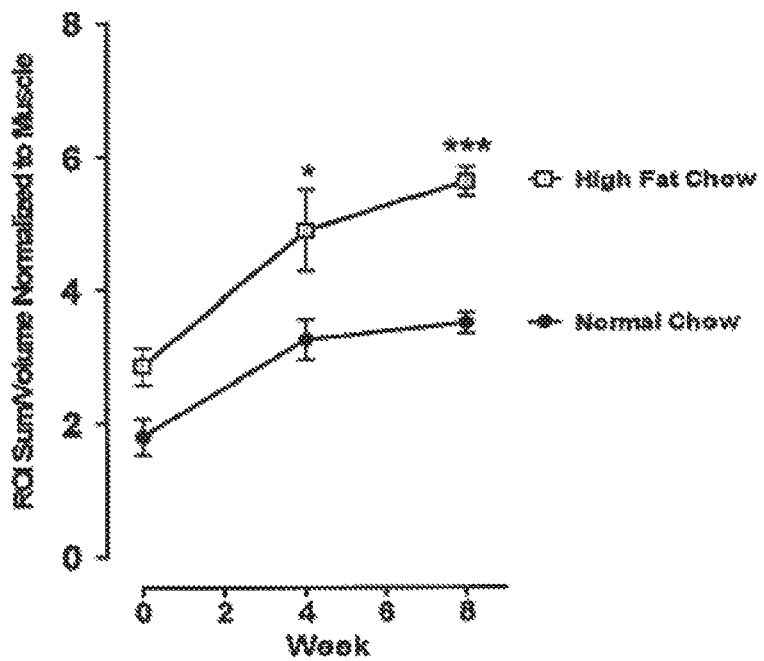
Figure 10C:
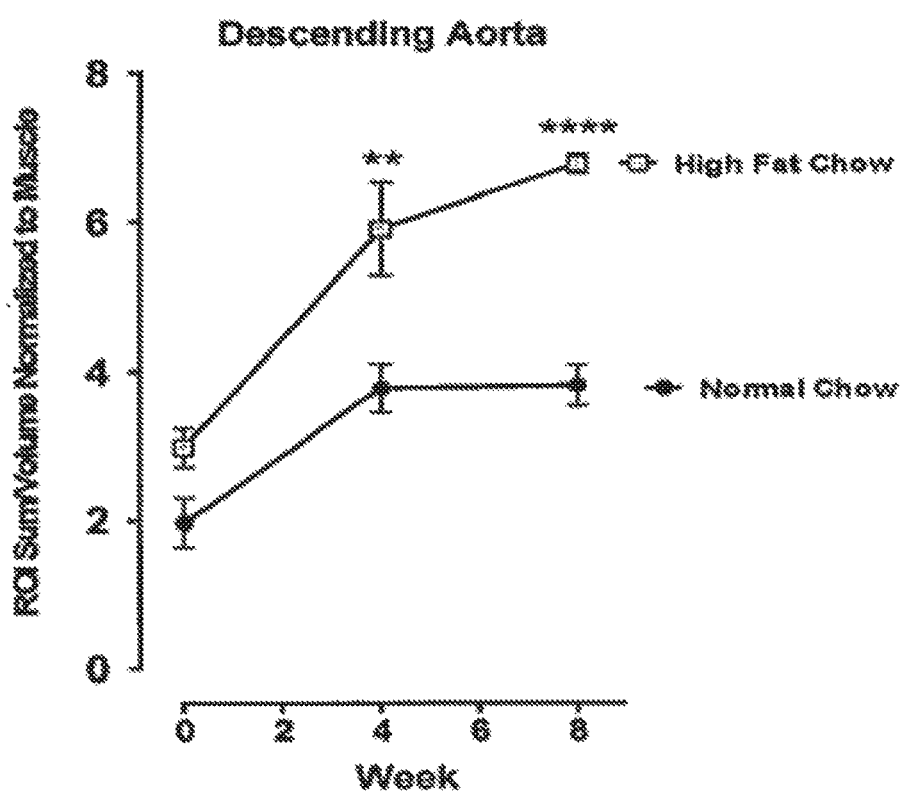
Figure 11:
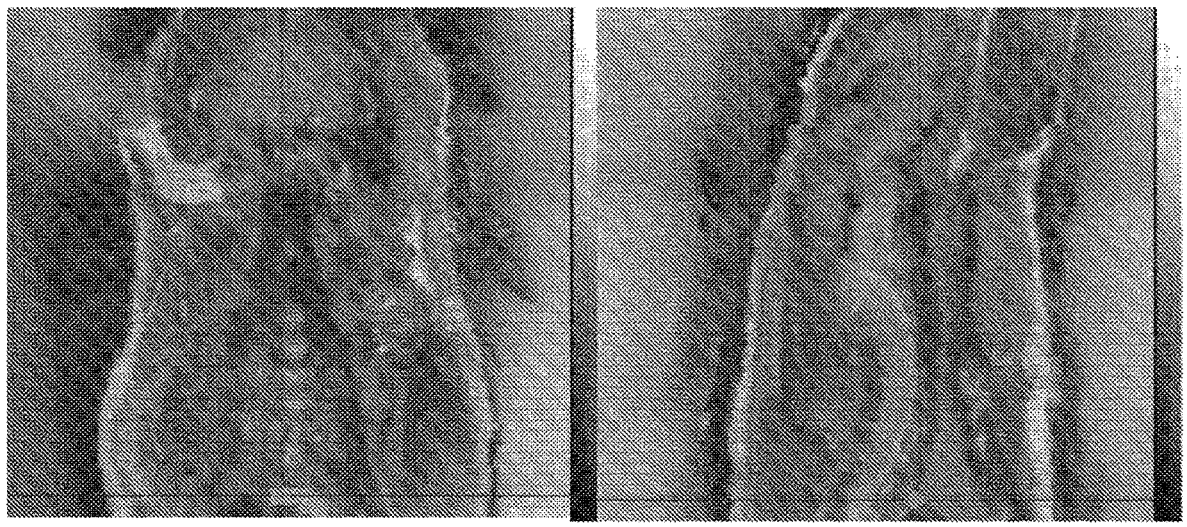
Figure 12:
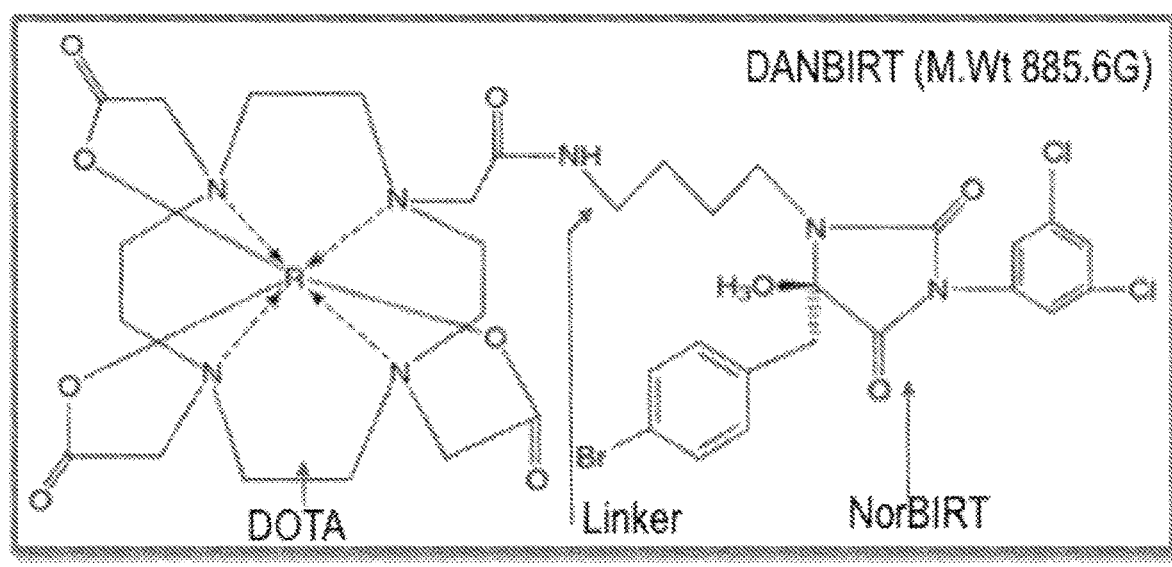
FIG. 12 shows the generic DANBIRT chemical structure and molecular weight.

24 hrs Autoradiography (FIG. 9, FIG. 11) and 3 hr SPECT/CT (FIG. 10) analysis correlated the findings and gave a clear idea towards the radioisotope distribution in cardiovascular tissue (heart, aortic arch, carotids). The results also showed increased uptake in the thymus, which would be consistent with increased immune response to vascular injury with a good anatomical correlation.

Discussion

Findings in SPECT/CT imaging and autoradiography correlate to bio distribution results having significant uptake in the thymus, heart, carotids, aortic arch and descending aorta, and also to serum and red blood cells with expected increase in uptake specifically in neutrophils (target population after ozone exposure, because of immediate acute immune response).

In vivo imaging model allowed to hypothesize that at this specific drug concentration there are high levels of a specific binding or saturation of binding sites to a point of complete occupancy that allows for free unbound compound in circulating blood volume and in other target organs and compartments; but knowing that our target has a very restricted expression to leukocytes.

At different drug concentrations specific binding to our target tissues (plaque leukocytes) is evidenced. Treatment groups did not show expected results in bio distribution assay, thereby impeding correlation of anti-lipidic and inflammatory effects. These groups were not included in our SPECT/CT analysis.

Conclusions

Serum lipid analysis and weekly growth analysis allowed us to conclude that the high fat diet worked by exponentially increasing cholesterol levels in exposed groups especially in LDL and VLDL levels and small sub particle levels which have been proven to increase atherosclerotic lesion development and disease evolution in ApoE KO models.

SPECT/CT imaging showed a longitudinal increase in uptake comparing high fat chow animals to normal chow animals along our different time points, being validated by Autoradiography analysis. ApoE KO animals being fed a Western diet show increased tissue uptake compared to animals that are ApoE KO mice but were fed a normal diet.

This example was a pilot study for implementation of this novel technology in different disease models. Further studies should assess vascular lesion characterization, plaque development and vascular remodeling in the disease model. But our next experiments (histology and whole blood concentration experiments) should confirm and will help validate $^{111}$In-DANBIRT as a diagnostic tool for inflammation assessment in cardiovascular injury models.

Example 3

Materials and Methods

Animals

Male Apo-E$^{-/-}$ mice on a C57BL/6 background (Taconic Laboratories, Indianapolis, Ind.) aged 6 weeks were housed two per cage and allowed to acclimate over the course of one week after delivery. Mice were fed either a normal chow diet or HFD (Harlan-Teklad, TD.88137: 1.5 g/kg of cholesterol and 42% kcal from fat) for 8 weeks; food and water were provided ad libitum. Food was changed every 3 days and stored at −20° C. and thawed before administration to the mice. For isolated blood distribution studies, male Sprague Dawley rats (Taconic Laboratories, Indianapolis, Ind.) aged 6-8 weeks were allowed 1 week of acclimation following delivery. Rats were housed two per cage and given food and water ad libitum. Both rats and mice were maintained on a 12 h light:dark schedule in AAALAC-approved facilities, and euthanized via cardiac exsanguination while under deep anesthesia with Isofluorane (Piramidal Healthcare, NDC 66794-093-25). The UNM Institutional Animal Care and Use Committee (IACUC) approved all procedures performed. Animal experimental design is summarized in FIG. 13, Table 1.

Serum Lipid Levels and Sub Particle Analysis

Mice were euthanized after 8 weeks of normal or HFD; whole blood was collected by direct cardiac puncture using a 24-gauge needle coated with 100 IU of Heparin (Sagent, WH0127N). Blood was centrifuged for 15 minutes at 1000 g at 4° C., serum was isolated from other blood components and transferred to individual Eppendorf tubes with no added anticoagulant and frozen at −20° C. Serum was analyzed for total cholesterol and triglyceride level, as well as size dependent sub-particle quantification (Skylight biotech, Liposearch).

Radiolabeling of DOTA-Alkylamino-NorBIRT (DANBIRT) with $^{111}$In and $^{68}$Ga DANBIRT was radiolabeled using either $^{68}$Ga or $^{111}$In with a determined specific activity of 625 mCi/pM and a concentration of 1 μg:1 μL. Indium chloride was obtained from Genera) Electric Radiopharmaceutical Department (GE Healthcare, INS.IPA) and $^{68}$Ga was eluted from an Eckert and Ziegler $^{67}$Ge/$^{68}$Ga generator using 0.01 M HCl. The pH was assessed for acidic concentration of radionuclide solution using a BAKER-pHIX color-fixed indicator stick (J. T. Baker, 4394-01) as well as activity and volume. The volume of stock solution necessary for desired labeling activity is calculated, buffer is added to the solution before adding DANBIRT. Amount of DANBIRT needed for every 4 mCi of $^{111}$In or $^{68}$Ga for radiolabeling was determined to be 6 μg of DANBIRT (M.W. 886.5 G/mole). The reaction vial is buffered using a pH range of 4.0-4.5 with addition of 4 mM ammonium acetate (J. T. Baker, 0599-08) for $^{111}$In and a pH of 4.5 for $^{68}$Ga. The reaction vial was heated in a hot block at 100° C. for 35 minutes, vortexing every 10 minutes. Quality assurance was performed with Instant thin layer chromatography (ITLC) and High Pressure Liquid Chromatography (HPLC) following methods by Poria et al [24].

In Vitro Stability of Radiolabeled DANBIRT

Incubation of [$^{68}$Ga] Ga-DANBIRT with Fetal Bovine Serum (FBS) (Atlanta Biologicals, S11150) and 0.9% saline solution was performed in vitro stability analysis. Triplicate samples were drawn from radiolabeled stock and kept incubated at 37° C. until time of analysis. ITLC was performed once at each time point and HPLC assessment was performed in triplicates at baseline, 5, 10, 30, 60, 120 and 240 minutes of incubation. The mean incorporation yield and radiochemical purity were calculated from sample results. Following methods by Poria et al [24] methods were modified for use in a Ultra-Performance Liquid Chromatography (UPLC) using an Acquity UPLC BEH C-18 1.7 μm column (2.1×50 mm) (Waters Corporation, 186002350). UPLC gradient with flow rate is described in FIG. 14. Table 2.

Biodistribution of [$^{111}$In] In-DANBIRT

Upon completion of 8 weeks on normal or HFD, mice were euthanized 3 hours post-injection of 700 μCi of [$^{111}$In] In-DANBIRT via tail vein; organs were harvested for weight assessment and [$^{111}$In] In-DANBIRT uptake using an Automatic Wizard 2 Gamma counter (Perkin Elmer). Organs collected were: tail, whole blood, aorta (from aortic arch to thoracic aorta), carotids (front aortic arch to bifurcation), heart, liver, muscle and adipose tissue. Whole blood was collected with direct cardiac puncture of right ventricle using a 24-gauge needle of right ventricle with a heparinized syringe and centrifuged for 15 minutes at 1000 g at 4° C. Serum, erythrocytes (RBC) and leukocytes (WBC) containing isolated samples were collected and measured for [$^{111}$In] In-DANBIRT uptake using a gamma counter. Uptake was decay-corrected and percent-injected activity per gram (% IA/gr) was determined for each mouse.

Ozone Exposure and Blood Component Distribution

Rats were exposed to either filtered air (FA) or ozone (1.0 ppm) for 4 hours using an OREC silent arc discharge ozone generator (Osmonics, Phoenix, Ariz.); ozone concentrations were continuously monitored over the course of 4 hours. Exposures took place in a chamber without bedding to minimize ozone scrubbing and to ensure consistent nasal exposures. Whole blood was collected 24 hours post-exposure. Histopaque two-step gradient (Sigma Aldrich, 10771) neutrophil isolation protocol was performed following manufacturer's methods; modified protocol was included for PBMC isolation. Hetastarch at 5% (B. Braun, L6511) was added to whole blood before running isolation protocols. Cell samples were washed and suspended in 1% Gelatin in PBS at a pH of 7.2. Final volumes of neutrophil and PBMC samples were increased to 1 mL. Final samples were identified as serum, RBC, neutrophils and PBMCs and incubated for 1 hour with [$^{68}$Ga] Ga-DANBIRT (specific activity of 625 mCi/pM). Sample smears were performed and stained with Wright-Giemsa horizontal staining protocol according to manufacturer instructions (Sigma Aldrich, SLBN4704V). Cell morphology, differentials and sample purity were assessed using a light microscope at 40× objective (Olympus BX51).

Radioisotopic Dilution Methods

Radioisotopic dilution methods were performed with log-fold serial dilutions at concentrations of 1:1, 1:10, 1:100 and 1:1000 radiolabeled DANBIRT. Rat whole blood was collected and incubated for 10 minutes with [$^{111}$In] In-DANBIRT. Leukocyte isolation was performed for neutrophil and PBMC separations post-incubation with radiolabeled DANBIRT (specific activity 625 mCi/pM). Cytospin 2 (Shandon 2,59900002) with double-funnel and white filter (Simport, 930941126) was used for clustered cell differentials identification methods. Cytospin samples were spread in Superfrost Plus slides (VWR, 48311-703) and fixed with 5% methanol. Wright-Giemsa horizontal staining protocol was performed according to manufacturer's package insert instructions (Sigma Aldrich, SLBN4704V). Cell morphology, differentials and sample purity were assessed using a light microscope at 40× objective (Olympus BX51).

3 Hr [$^{111}$In] In-DANBIRT SPECT/CT Imaging and Analysis

Animals were imaged at 0.4 and 8-weeks following 700 µCi via tail vein injection of [$^{111}$In] In-DANBIRT. Imaging was performed using 45 minute acquisitions on a NanoSPECT/CT® dedicated small-animal imaging system (Bioscan, Inc. Washington, D.C.) with specific topogram and SPECT parameters (FIG. 16, Table 3) while animals were in deep anesthesia with isofluorane (Piramidal Healthcare, NDC 66794-093-25). Regions of Interests (ROI) were determined and drawn using the best quality image phantom from reconstructed CT (Table 3) to determine muscle, adipose, heart, aortic arch and descending aorta organs using VivoQuant 2.00 (inviCRO, Boston, Mass.). The ROI were extrapolated from phantom scan image onto every image and adjusted according to specific morphologic parameters. Concentration and sum per volume normalized to muscle was determined to identify accurate measurements and eliminate ROI signal interference from adjacent tissues. Activity was decay corrected and compared between and among dietary groups.

24-Hour [$^{111}$In] In-DANBIRT 3D Autoradiography and Image Analysis

Mice were euthanized by $CO_2$ method after 8 weeks of dietary assessment. After removal of limbs, ears, tail and whiskers carcasses were individually frozen in a hexane/dry ice bath and embedded vertically in a mold by adding an aqueous solution of 5% carboxymethylcellulose sodium salt (CMC) (C5678, Sigma, St. Louis Mo.) in a hexane/dry ice bath. Block was stored at least 12 hours at −20° C. prior to removal from mold and mounting on a specimen stage in the cryomacrotome (Leica CM3600 X, Leica Biosystems, Nussloch, Germany). Multiple ⅛-inch holes were drilled in the CMC block adjacent to the carcasses and filled with a solution of black India ink and $^{14}$C (1 µCi/mL) to provide registration marks to allow linking the white light block images with the autoradiography images. The carcasses were cut in 50 µm sections in the vertical plane, starting from below the ear location. Prior to cutting each section, a digital photo was taken (Canon EOS 70D Focal Length of 35 mm, Melville, N.Y.) of the block surface. Every 10 slices, a section was transferred to 2.5 mm Label Guard Protection Tape (Scotch 3M 821, DeKalb, Ill.) and dehydrated in the cryomacrotome for a minimum of 24 hours. After a total of 55 sections, autoradiography was taken and accompanied by approximately 600 white light photos. Cryosections were removed and mounted on black cardboard along with a set of calibration standards prepared from the radiolabeled DANBIRT, serially diluted in 1% CMC, and sectioned from a separate block. Dehydrated sections were covered with 1.4 µm Isotope Imaging Film (FlushTec, Hemet, Calif.) and placed on Fujifilm Imaging Plates (BAS-IP SR 2025, GE Healthcare, Piscataway, N.J.) and exposed for 24 hours in a lead chamber (Raytest, Straubenhardt, Germany) with 0.04" lead sheeting between each screen cassette. Screens were imaged on a Phosphorous Imager Typhoon FLA 7000 (GE Healthcare, Piscataway, N.J.). Autoradiography and white light files were compiled and analyzed using VivoQuant 2.00 (inviCRO, Boston, Mass.). Determined ROI were drawn using the best quality image phantom from reconstructed CT (FIG. 14, Table 3) for the thymus, muscle, carotids and aortic arch. The ROI were extrapolated from phantom scan into every image and adjusted according to specific morphologic parameters.

Histologic Analysis

ApoE$^{−/−}$ mouse hearts were collected, perfused and snap frozen in liquid nitrogen and stored at −80° C. The upper third of the heart with the aortic outflow tract were mounted in optimal cutting temperature (OCT) compound for sectioning. Cryosectioning was performed on OCT heart blocks using a Leica CM 3050S Cryostat at −20° C. for collection of 10 µm sections from the subaortic leaflet region. For Oil Red O staining (Sigma-Aldrich, O0625, SLBP5248V), slides were left at room temperature for 10 minutes and incubated with Oil Red O working solution and counterstained with Mayer's hematoxylin (Sigma-Aldrich, SLBPG176V) following manufacturer's staining protocol. Surface lesion area and arterial vessel circumference were quantified using Olympus cellSens Standard 1.13 to calculate percentage of atheroma lesion area by arterial wall circumference. Quality control assessment was performed to compare intensity of Oil Red O staining between groups.

Immunohistochemistry

The OCT embedded frozen sections (10 µm) were fixed in methanol for 10 minutes at −20° C. After washing in PBS, the sections were incubated with fluorescein isothiocyanate (FITC) conjugated rat anti mouse CD11a (SouthernBiotech S1555-02) antibody (1:250) for 2 hours in a humidifier chamber. Sections were counterstained with DAPI (1:1000 dilution), imaged at 10× and 63× using a Fluorescence Microscope (Zeiss AxioObserver-Hamamatsu Flash4.0 sCMOS Monochrome Camera), image reconstruction was performed under FITC (490 Ex, 525Em) channel. Image processing was performed using Olympus cellSens Standard 1.13.

Statistical Methods

All statistics were computed using two-tailed Student's t-tests, or one-way and 2-way factorial ANOVA. Tukey's post-hoc test and Sidak's correction test were used for multiple comparisons. Resulting p-values <0.05 were considered significant. The results from 3D autoradiography results were compared as a mean difference in quantitative uptake reflected as % IA/gr normalized to muscle of radiolabeled DANBIRT because of limitations in compatibility of $^{111}$In radioactive standards in this pilot study. GraphPad Prism 6.0 software for mac (GraphPad Software, Inc.) was used for all statistical analyses.

Results

Radiolabeling and in Vitro Characterization of [$^{111}$In] In-DANBIRT

Figure 16:
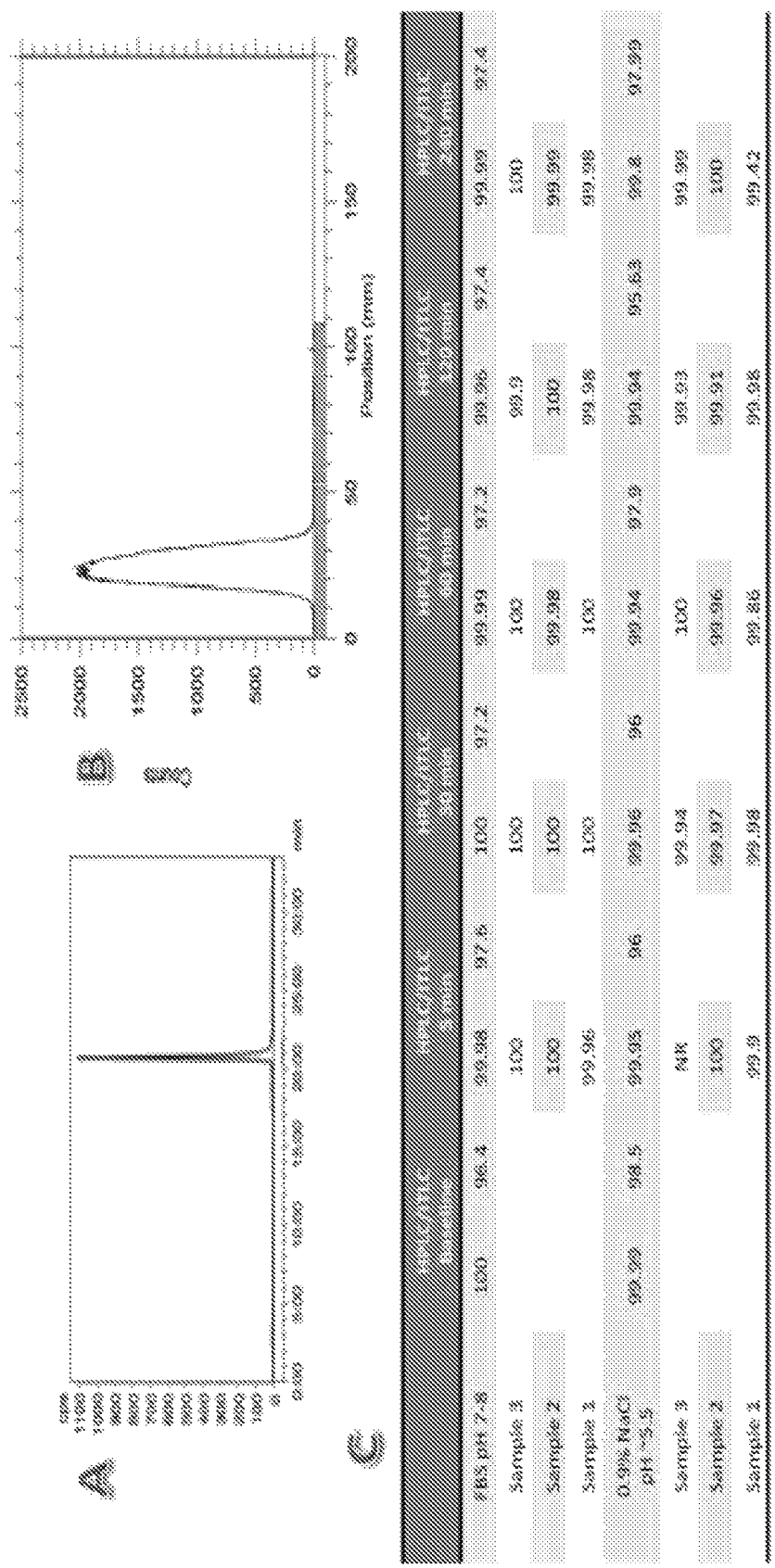
FIG. 16 shows the radiolabeled DANBIRT in vitro stability. Representative HPLC (A) and ITLC (B) results were performed to assess in vitro stability after radiolabeling protocol for $^{68}$Ga was completed. (C) Incubation in fetal Bovine Serum (FBS) and 0.9% Saline solution showed >95% mean radiochemical purity and incorporation yield in triplicate samples at baseline, 5 minutes, 30 minutes, 60 minutes, 120 minutes and 240 minutes of incubation.

DANBIRT was efficiently labeled for experiments using $^{111}$In and $^{68}$Ga, achieving high in vitro stability. Assessment reflected >99% incorporation yield by ITLC and >99% radiochemical purity by HPLC analysis. Triplicate serial samples of radiolabeled DANBIRT incubated with fetal bovine serum (FBS) and 0.9% saline solution showed >95% mean radiochemical purity using UPLC method and >97% mean incorporation yield using ITLC method. Stability of [$^{111}$In] In-DANBIRT was maintained throughout 4 hours of incubation (FIG. 16).

Ex Vivo Biodistribution of [$^{111}$In] In-DANBIRT Post Tail Vein Injection

From biodistribution analysis of [$^{111}$In] In-DANBIRT, liver samples showed high uptake when compared to other tissues regardless of dietary treatment. Liver inspection after dissection revealed a pale white color with fibrous consistency in all HFD fed mice but not evident in normal diet fed mice, suggestive of steatosis. Serum samples also showed a high uptake compared to other blood components, similar only of those levels from liver samples. Cardiovascular tissues (heart, aorta, carotids) reflected higher uptake in animals that were fed a HFD (p<0.05).

Figure 17:
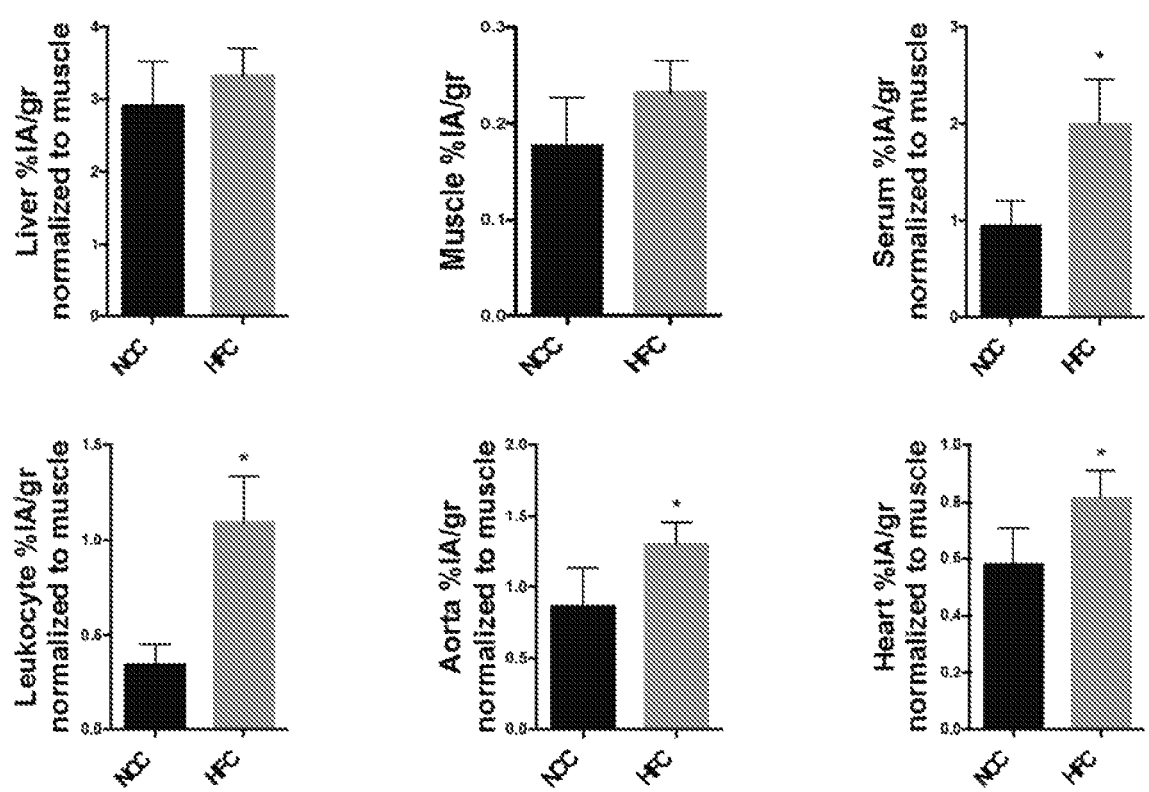
FIG. 17 shows the biodistribution analysis of [111In] In-DANBIRT on ApoE$^{-/-}$ mice after 8 weeks of dietary assessment. Muscle, heart, aorta, serum, WBC and liver were harvested and uptake was quantified. Results showed higher uptake in cardiovascular tissues and leukocytes in mice that were fed a HFD (p<0.05).

Similar findings were found in RBC and WBC samples with increased uptake in HFD fed mice compared to normal diet fed mice (p<0.05) (FIG. 17). Distribution of [$^{111}$In] In-DANBIRT showed an increase in % IA/gr of tissue in animals that were fed a HFD in comparison to animals fed a normal fed diet (p<0.05).

Metabolic Effects in ApoE$^{-/-}$ Mouse Model After 8 Weeks of HFD

Figure 18:
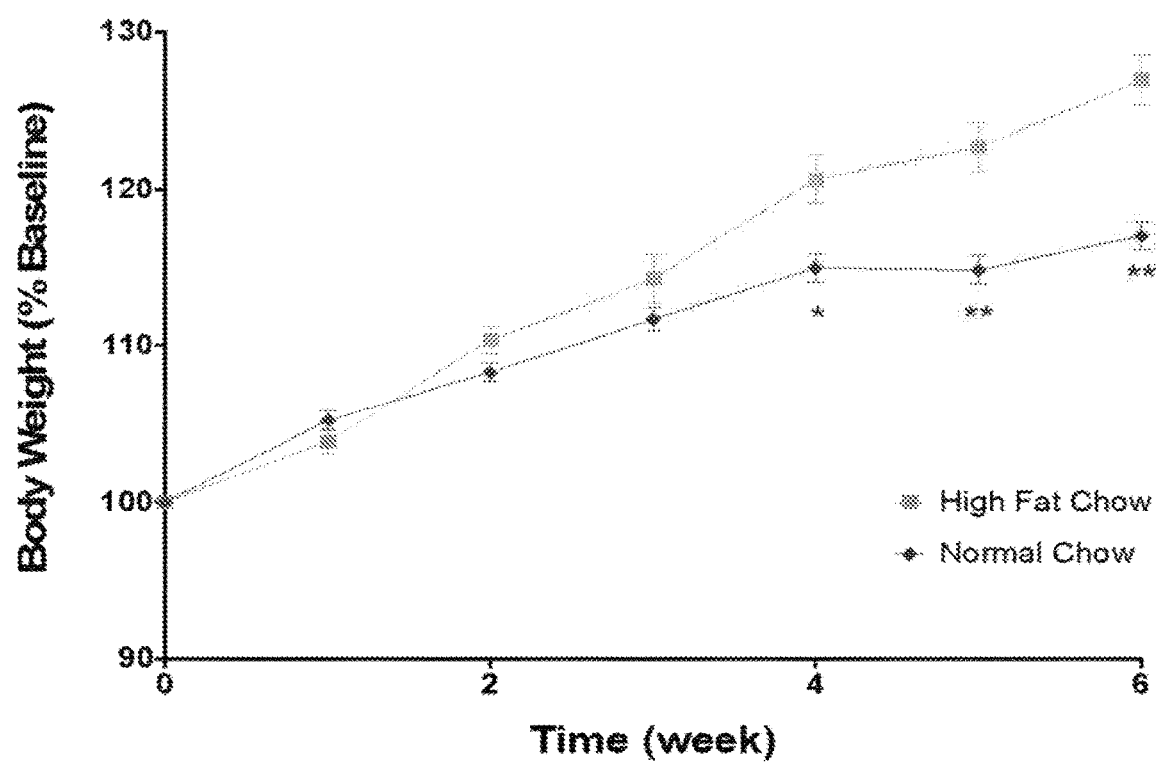
FIG. 18 shows the percentage weight gain per week from baseline weight of ApoE$^{-/-}$ mice after 8 weeks of dietary assessment. Percentage of baseline body weight increase compared at weekly time points represented as weeks per dietary group.
Figure 19:
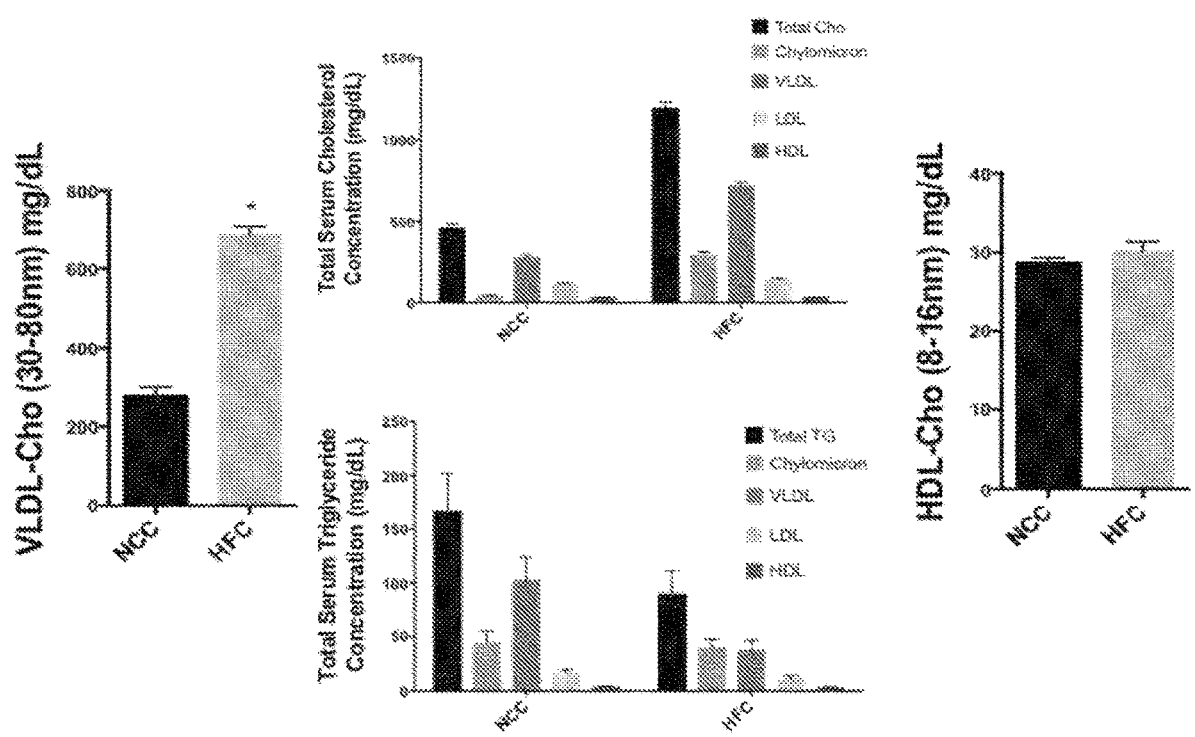
FIG. 19 shows the serum total cholesterol and triglyceride level quantification in ApoE$^{-/-}$ mice per dietary group. Total cholesterol, total triglyceride, VLDL, HDL, LDL and chylomicron quantification are expressed as concentration in milligrams per deciliter (mg/dL) and in nanometers (nm) for panicle size.

Biological model was guided by mice Apolipoprotein E deficiency placed on a HFD, resulting in an increased percent weight gain per week compared to animals in a normal diet (p<0.05) (FIG. 18). Serum lipid levels and subparticle analysis showed that total cholesterol levels were higher in HFD fed mice, and higher levels of total triglycerides in normal diet fed mice; VLDL-Cholesterol and HDL-Cholesterol were also statistically different between dietary groups (p<0.05) (FIG. 19). These results confirm the dietary effects in this model.

Figure 20:
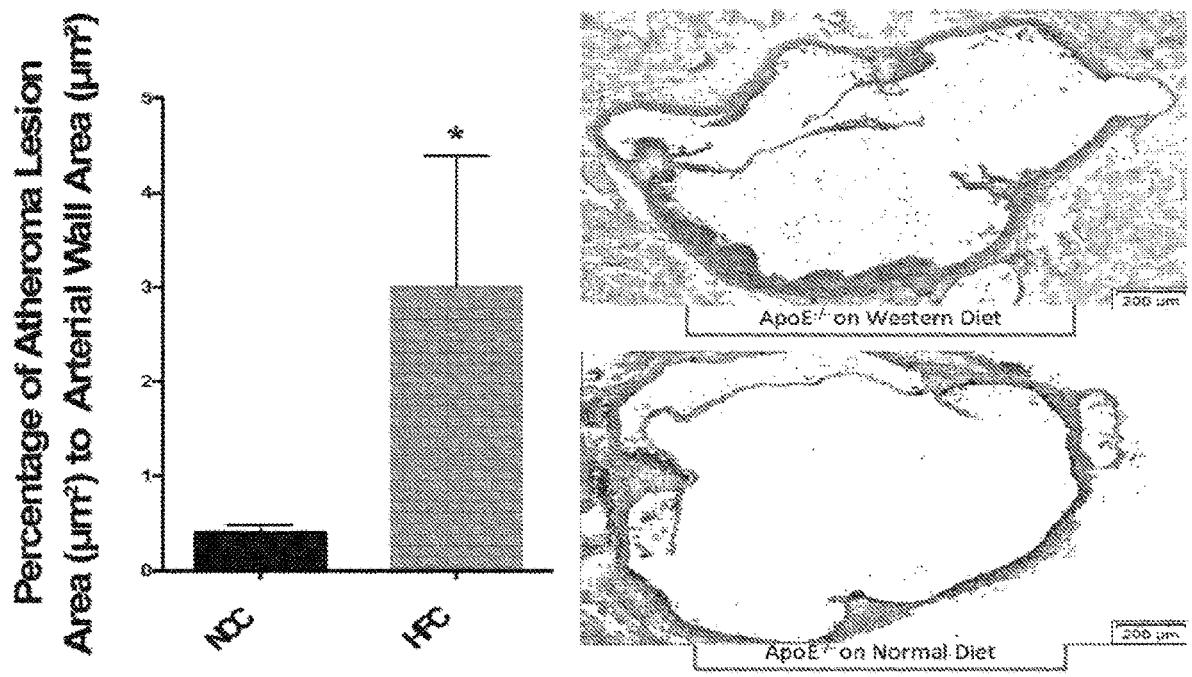
FIG. 20 shows the histologic analysis of OCT frozen subaortic leaflet atherosclerotic lesions. Oil red O staining of histologic sections of OCT frozen subaortic leaflet atherosclerotic lesions under a 10× objective, represented as percentage of atheroma lesion area to arterial vessel wall area ($\mu m^2$) per dietary group.

Histologic and Immunohistochemical Analysis of Aortic Atherosclerosis Development Histologic analysis reflected an accumulation of inflammatory tissue in the subaortic leaflet region of Apo$^{-/-}$ mice. Histologic analysis of OCT frozen cryosections showed a higher percentage of atherosclerotic lesion area in relationship to vessel wall area in HFD fed mice compared to normal chow fed mice (p<0.05) which were correlated by Oil Red O staining for lipid accumulation. Oil red O staining quality control and assessment also reflected higher intensity of tissue staining area in HFD fed mice compared to normal fed mice (FIG. 20).

Figure 21:
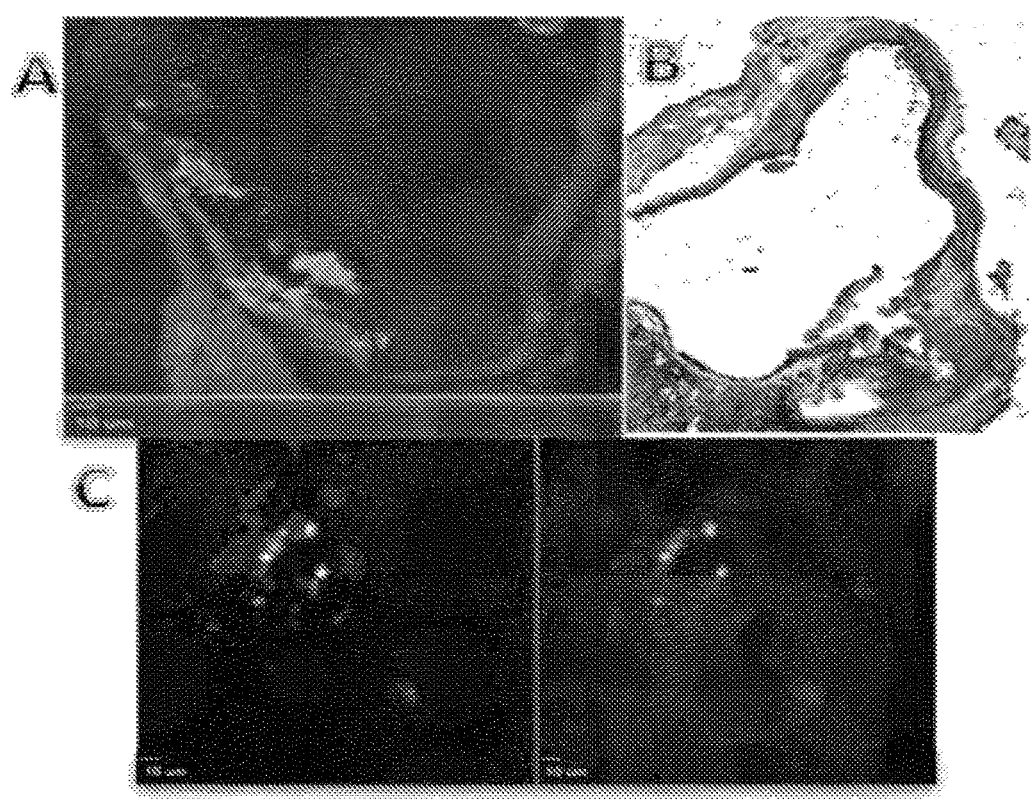
FIG. 21 shows the immunohistochemistry of OCT frozen subaortic leaflet atherosclerotic lesions. (A) FITC conjugated rat anti-mouse CD11a (10× objective) (B) compared to Oil Red O staining of consequent slides in HFD fed animals (10× objective). (C) Subaortic vessel wall leaflet atherosclerotic lesions stained with FITC conjugated rat anti-mouse CD11a (63× objective w/immersion oil).

Immunohistochemistry was performed using anti-CD11a (LFA-1) antibody to identify qualitative atherosclerotic intraplaque CD11a leukocytes (FIG. 21).

Figure 22:
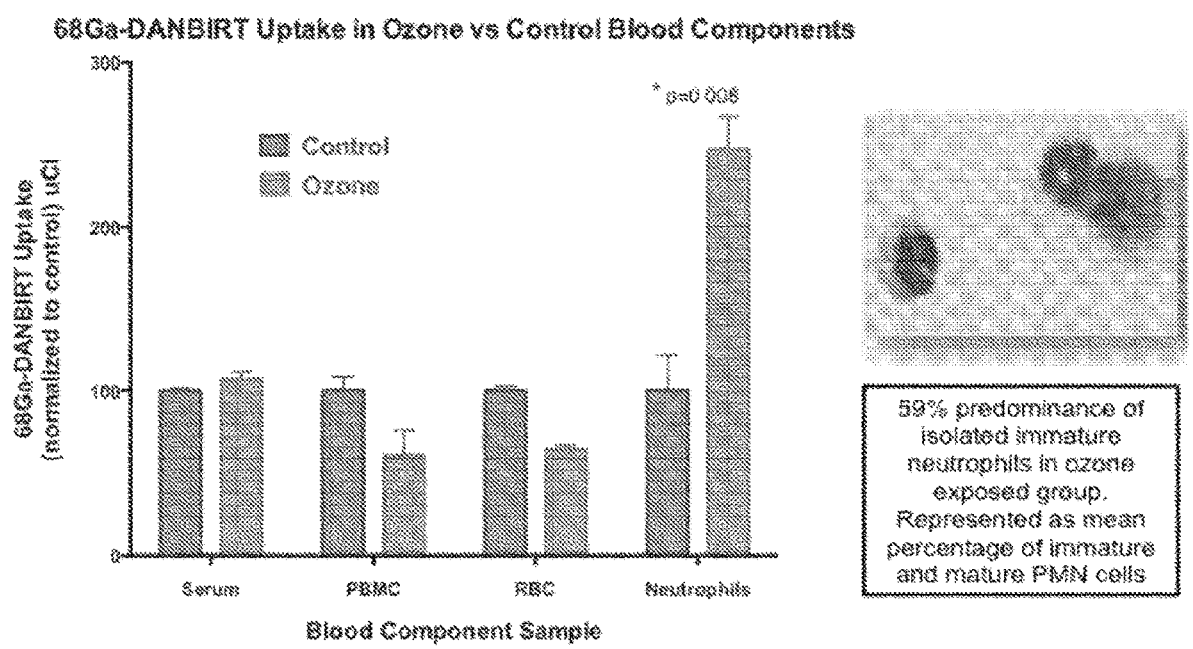
FIG. 22 shows radiolabeled DANBIRT uptake in isolated blood components post 4-hour exposure to ozone. Data showed an increased uptake of [$^{68}$Ga] Ga-DANBIRT in neutrophils post 4-hour ozone exposure (*p=0.008) with a decrease in PBMC and serum uptake. Cytospin slides were stained using Wright-Giemsa horizontal method for differential analysis of isolated sample purity under 100× objective w/immersion oil with a light microscope.
Figure 23:
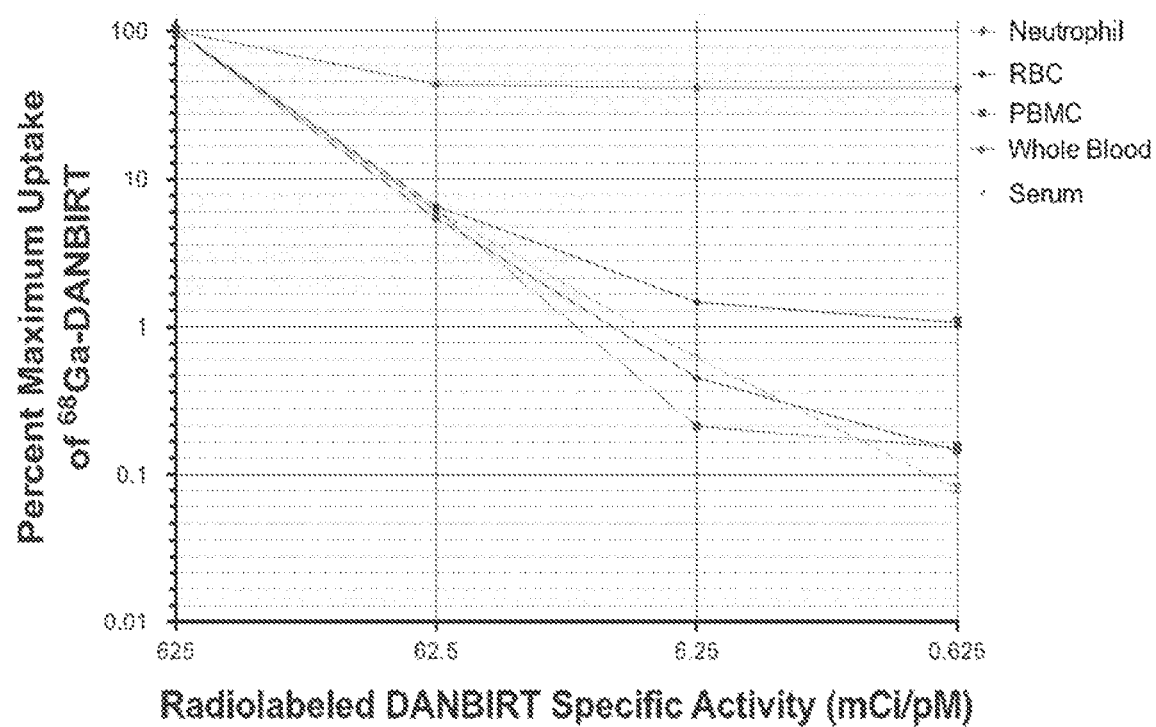
FIG. 23 shows radiolabeled DANBIRT competitive binding assays. Radioisotopic dilution methods were performed using an initial specific activity of 625 mCi/pM and consequent serial log-fold dilution concentrations. Saturation of isolated neutrophils as of percent of maximum uptake was observed starting at 62.5 mCi/pM (1:10× log fold dilution concentration) specific activity of radiolabeled DANBIRT.

LFA-1-Specific Targeting and Competitive Leukocyte Binding with Radiolabeled DANBIRT Leukocyte isolation methods successfully identified purity of samples, with predominance of immature neutrophils (~59%) and PBMCs (~53%) in ozone-exposed rats (used to induce a circulating neutrophilia, as previously described[25]) with no other relevant morphologic cell changes. Data showed an increased uptake of [$^{68}$Ga] Ga-DANBIRT in neutrophils (*p=0.008) (FIG. 22), with a decreased uptake in PBMCs post-ozone exposure. Log-fold dilution concentrations of [$^{111}$In] In-DANBIRT identified a competition for LFA-1 receptor binding in target leukocytes. Incrementing radiolabeled DANBIRT concentration resulted in competitive binding, identifying a saturation of binding sites in neutrophils starting at a 1:10 log-fold serial dilution concentration of [$^{111}$In] In-DANBIRT (FIG. 23). A pattern of 50% decreased initial uptake after each log fold dilution concentration was evidenced in serum, RBC and PBMC samples. PBMCs at different dilution concentrations did not evidence any saturation levels or reflected a tendency when compared to neutrophil sample (p<0.05).

Figure 24:
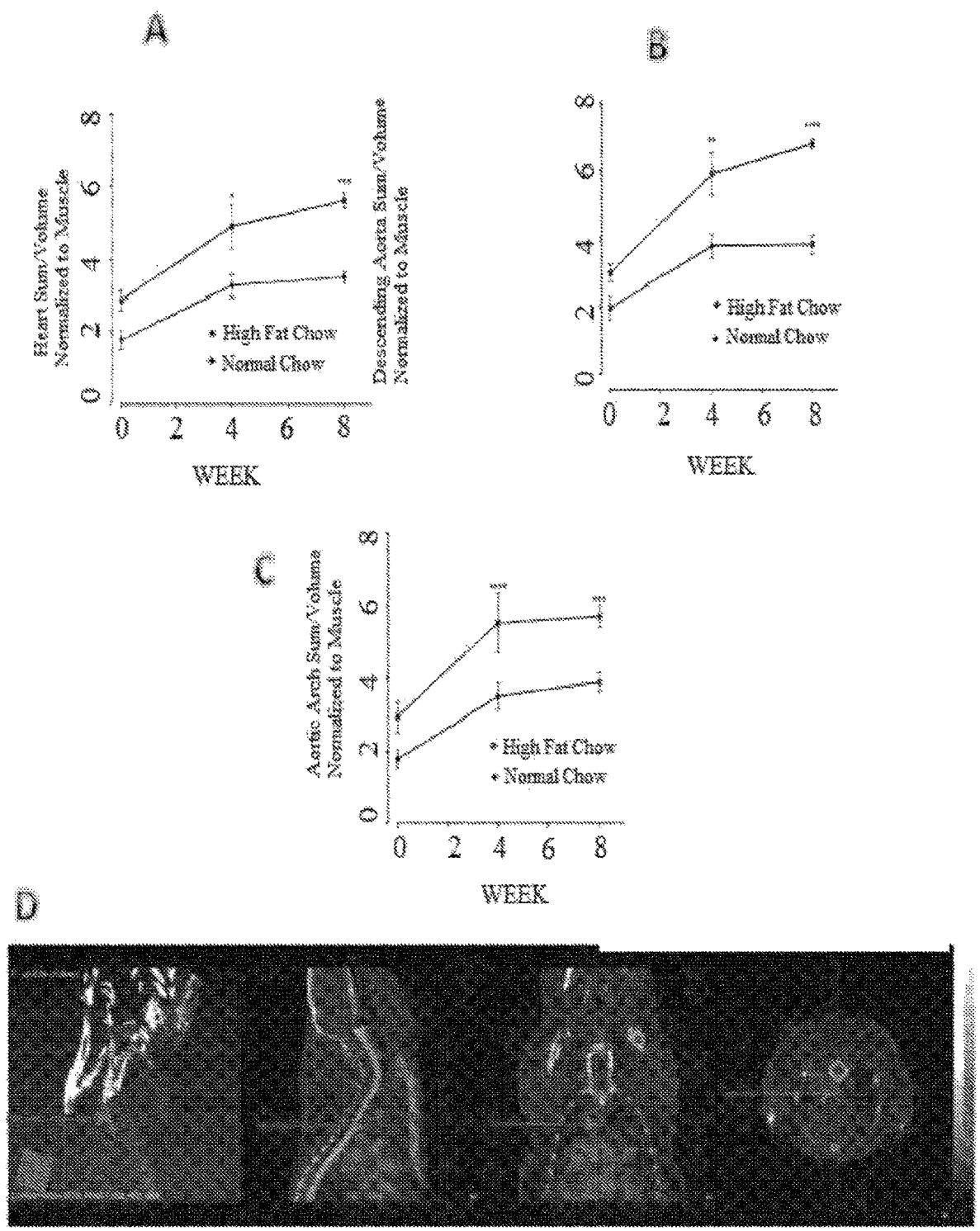
FIG. 24 shows 3 hr [111In] In-DANBIRT SPECT/CT imaging. (A, B, C) Increased longitudinal uptake of [111In] In-DANBIRT in cardiovascular areas prone to vascular atherosclerosis development (heart, descending aorta, aortic arch) reflecting a longitudinal increase per time point (week) shown by SPECT/CT imaging. (D) ROI were drawn for muscle, descending aorta, aortic arch and heart using VivoQuant (inviCRO) from phantom scan and extrapolated in each subject. Red arrows point to ROI of descending aorta.
Figure 25:
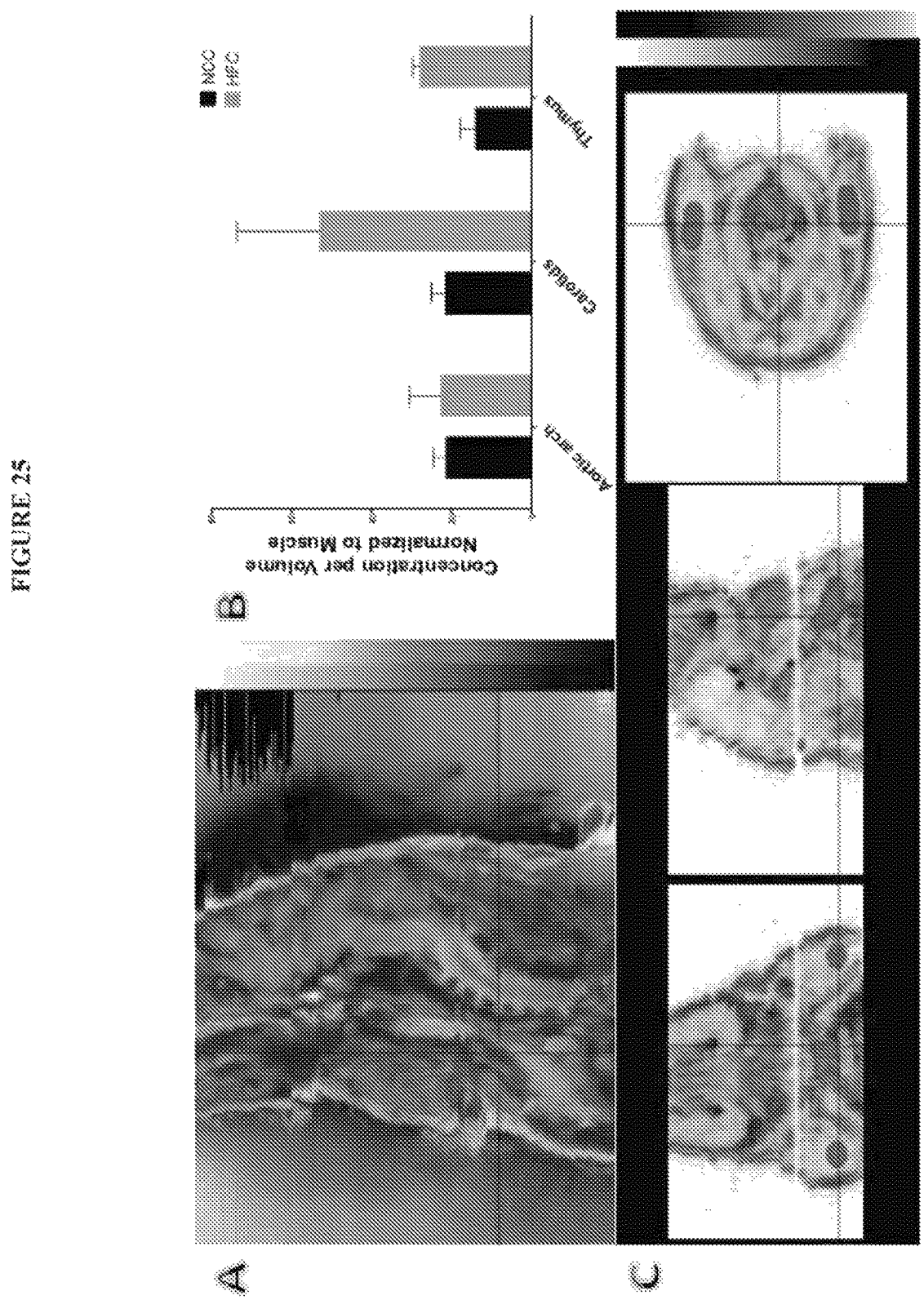
FIG. 25 shows 24 hr [111In] In-DANBIRT 3D autoradiography. (A,C) ROI were drawn for muscle (blue), common carotids (green), aortic arch (cyan) and thymus (red) using VivoQuant from phantom scan and extrapolated in each subject, reflecting concentration per volume normalized to muscle. (B) Increased uptake of [111In] In-DANBIRT in common carotids and thymus in HFD fed mice compared to normal diet fed mice.

Longitudinal Molecular Imaging of Cardiovascular LFA-1 Presence with [$^{111}$In]In-DANBIRT The 3 hr [$^{111}$In] In-DANBIRT SPECT/CT imaging showed a longitudinal increased uptake in heart, aortic arch and descending aorta ROI concentration quantification in the 4th and 8th week time points in HFD fed mice (FIG. 24). The 24 hr [$^{111}$In] In-DANBIRT 3D autoradiography allowed a functional and more advanced anatomical assessment of the presence of inflammatory LFA-1 in immune and cardiovascular tissues, an essential finding to characterize the biological model. Mice fed exhibited an increase in carotids and thymus's concentration per volume normalized to muscle in HFD ted mice compared to normal diet fed mice (FIG. 25).

Discussion

The purpose of this study was to determine the value of [$^{111}$In] In-DANBIRT as a non-invasive in vivo imaging tool for LFA-1 expression in leukocytes in the inflammatory process of atheroma development by longitudinal SPECT/CT molecular imaging. Results showed that we were able to target the increased LFA-1 expression in neutrophils under an acute systemic immune injury model (i.e., ozone exposure), used analogously to early inflammatory developmental stage of vascular atherosclerotic lesions. Longitudinally-increased uptake in cardiovascular tissues, shown by SPECT/CT, illustrates the translational component and value in a chronic model. In vivo assessment of atherosclerotic plaque vulnerability is a clear need in cardiovascular research. Biotechnological approaches designed to identify, assess, and potentially eliminate fatal repercussions of atheroma development could have great benefits to patients [26]. Longitudinal in vivo imaging of plaque inflammatory processes is a very promising concept to advance understanding and reduce cardiovascular related complications [27].

The selective expression of LFA-1 in leukocytes and DANBIRT's small size contribute to a theoretically ideal imaging probe of inflammatory activity inside of the plaque. LFA-1/ICAM-1 complex is important in almost every vascular disease because of its role in leukocyte recruitment and transmigration[28]. T-cell activation and migration to sites of inflammation is guided predominantly by LFA-1/ICAM-1 interaction and Signal-2[29], making the allosteric inhibition of LFA-1 an effective way to target intraplaque inflammation[24]. Recent papers address the functionality and sensitivity of LFA-1, understanding that modulation of this integrin will impact immune progression of disease[30]. Atherosclerosis development is dependent on the severity of the immune response at sites of vascular injury, along with the ability to resolve such inflammation [31]. Inflammatory components such as leukocytes have major roles in plaque vulnerability and instability, impacting barrier integrity, releasing peptidases that facilitate remodeling, and generating pro-inflammatory chemokines. Local and systemic immune response appears to guide cardiovascular tissue uptake [32], while illustrating the potential for enhancing SPECT/CT interpretative results in a more sensitive and specific system. Numerous in vivo imaging strategies are being assessed for effective diagnosis of atherosclerotic plaque vulnerability. Many other studies have characterizes the unique plaque characteristics, such as calcium presence and morphology, without fully addressing the role of neutrophil accumulation in the plaque. Work performed with DANBIRT and the detection of vascular LFA-1 levels stands as an attempt to complement other imaging approaches. Novel approaches utilizing enhanced hybrid imaging systems that target metabolic activity inside of the plaque to assess glucose uptake in such tissues may further add to a battery of plaque characteristics that can be more precisely linked to adverse pathological outcomes [33]. Understanding the role of neutrophils in plaque vulnerability is important[17], because of the correlation between plaque instability and the presence of neutrophil-derived acute immune response markers.

From results we know that radioisotopic dilution methods helped us achieve a concentration in which the observe competitive binding[34] illustrated receptor saturation in neutrophils. Saturation in these samples correlates to findings in the biodistribution and post-ozone exposure data, confirming the role of [$^{111}$In]-DANBIRT for radiolabeling neutrophils at a proven specific activity and concentration. The increased volume from serum and RBC samples did not reflect nonspecific binding in these experiments, but did explain the concept of saturation of LFA-1 binding sites in neutrophils. Another important characteristic of $^{111}$In (Indium chloride, chemical presentation provided by GE Healthcare) is that it has high uptake in the liver and lungs because of binding interaction with transferrin and lactoferrin[35] illustrating initial biodistribution high uptake levels in the liver. These studies effectively demonstrated radiolabeling of DANBIRT using $^{68}$Ga (short-lived PET radioisotope) and $^{111}$In (longer-lived SPECT radioisotope) demonstrating high stability throughout 4 hours of incubation in FBS and 0.9% NaCl. Through in vitro stability studies and effective labeling methods it is possible to safely administer $^{111}$In-DANBIRT intravenously as a stable radioligand probe.

The biodistribution of [$^{111}$In] In-DANBIRT showed a high uptake in the liver, serum and RBCs, which identified an issue with the binding potential was postulated as nonspecific uptake due to the mass effect of the radioligand specific activity. Adipose tissue and muscle were identified as potential low uptake tissues. Tissues surrounding the vessel lamina adventitia have been recently identified as sites of accumulation of inflammatory cells in ApoE$^{-/-}$ mice on a normal diet[36]. This effect was not clearly identified in the studies due to the limits of spatial resolution of the SPECT imaging system. However, adipose tissue was identified as lacking significantly different uptake compared to the tissue designated as background (muscle). These biodistribution results to hypothesize three specific scenarios: no binding, a specific binding or free, unlabeled drug. In vitro stability studies showed that at 4 hours post incubation in FBS and 0.9% NaCl, the radiolabeled DANBIRT was stabile, eliminating the possibility of free unlabeled drug/ligand post administration. By blood component isolation and post-ozone environmental exposure, the target cells were visualized in a proven animal model correlating with local and systemic acute immune response reflected parallel results from an innate immune response in the targeted cells[37].

Molecular imaging shows a longitudinally-increased uptake in cardiovascular tissues in mice fed a HFD, which correlates to atherosclerotic development because of the presence of shear stress areas in principal arterial vessels [38]. Functional and morphological assessment of [$^{111}$In] In-DANBIRT guides the translational component of probe development.

The limitations of these studies included reduced statistical power of the animal sample, although this was lessened due to the longitudinal collection of repeated measures data by SPECT/CT. Many mouse models use an ApoE$^{-/-}$ model of atherosclerosis development because of the resultant hypercholesterolemia and spontaneous presentation of plaque starting at 3 months of age[11]. The HFD increases the amount of plaques by 14 weeks of age[39]. Although deficiency of the LDL receptor will also cause high levels of lipids and some spontaneous diet-dependent plaques, the extent and slow progression of Ldlr deficiency makes the ApoE$^{-/-}$ model a desireable choice. The use of the wild type control strain (C57BL/6) was not considered as these mice fail to develop any observable vascular pathology. In a translatable approach, humans with hereditary hyperlipidemia have associated mutations of Ldlr and/or ApoE, which has been shown to increase the susceptibility to developing atherosclerosis[40]. Human atherosclerotic plaques resemble the ApoE$^{-/-}$ mouse model but, the Ldlr deficient mouse model develop a closer resemblance in the Epidemic panel in humans[41].

From these results, the development of early stage atheroma is includes acute inflammatory components. Histologic and immunohistochemical analysis supports the findings by characterizing the early development of the atherosclerotic model. The increased areas of atherosclerotic lesions and lipid accumulation correspond to results found in the HFD-fed animals. [$^{111}$In] In-DANBIRT is a promising radioligand for identification of the presence of LFA-1 in circulating leukocytes. Accumulation of immune cells in atherosclerotic plaque lesions mediates disease progression and vulnerability. Vascular atherosclerotic lesions in areas prone to atheroma development can be characterized by radioligand uptake. Thus, these findings support future investigation of a more advanced vascular disease model that will validate [$^{111}$In] In-DANBIRT as a diagnostic tool for assessment of inflammation in cardiovascular injury models.

Conclusions

Characterization of the biologic model identified the early stage development of atherosclerotic plaque in cardiovascular tissues with an acute inflammatory component. The longitudinally increase in [$^{111}$In] In-DANBIRT uptake in cardiovascular tissues in mice fed a HFD was consistent with histopathologically-observed advancement of aortic lesions. Neutrophil and PBMC isolation methods demonstrated selective and competitive LFA-1 antigen receptor binding in leukocytes. Radiosotopic dilution and receptor-binding assays evidence a mass effect in neutrophils with radiolabeled DANBIRT at a specific activity of <62.5 mCi/pM. These correlative results demonstrate competitive and specific LFA-1 antigen receptor binding to targeted leukocytes.

This study validates the potential of [$^{111}$In] In-DANBIRT to competitively bind leukocytes, especially neutrophils, while illustrating the presence in cardiovascular and immune tissues identified in a systemic inflammatory response following exposure to inhaled ozone. Recent publications corroborate BIRT377 as a potential drug for clinical applications in high-risk populations[21,24]. Further studies are needed to determine the value of this radioligand probe as an in vivo non-invasive imaging tool in an enhanced chronic vascular injury model exhibiting predominance of adaptive immunity components.

REFERENCES CITED

1. Arai, Y., et al., *Long-Term Effect of Lipid-Lowering Therapy on Atherosclerosis of Abdominal Aorta in Patients with Hypercholesterolemia: Noninvasive Evaluation by a New Image Analysis Program*. Angiology, 2002. 53(1): p. 57-68.
2. Blackwell D L, L. J., Clarke T C, *Summary health statistics for U.S. adults: National Health Interview Survey*. National Center for Health Statistics, 2012. Vital Health Stat 10(260).
3. Bykov, A. T., et al., [*Early diagnostics, prophylaxis, and non-pharmacological treatment of the preclinical stages of atherosclerosis and arterial hypertension*]. Vopr Kurortol Fizioter Lech Fiz Kult, 2015. 92(5): p. 18-21.
4. Jie Sun, M., et al., *Subclinical Carotid Atherosclerosis: Short-term Natural History of Lipid-rich Necrotic Core—A Multicenter Study with MR Imaging*. 2013.

5. Choi, S. Y. and G. S. Mintz, *What have we learned about plaque rupture in acute coronary syndromes?* Curr Cardiol Rep, 2010. 12(4): p. 338-43.
6. ten Kate, G. L., et al., *Molecular imaging of inflammation and intraplaque vasa vasorum: a step forward to identification of vulnerable plaques?* J Nucl Cardiol, 2010. 17(5): p. 897-912.
7. Hansson, G. K., A. K. Robertson, and C. Soderberg-Naucler, *Inflammation and atherosclerosis.* Annu Rev Pathol, 2006. 1: p. 297-329.
8. Imanaka-Yoshida, K., *Tenascin-C in Cardiovascular Tissue Remodeling.* Circulation Journal, 2012. 76(11): p. 2513-2520.
9. Nakata, Y. and N. Maeda, *Vulnerable atherosclerotic plaque morphology in apolipoprotein E-deficient mice unable to make ascorbic Acid.* Circulation. 2002. 105(12): p. 1485-90.
10. Johnson, J., et al., *Plaque rupture after short periods of fat feeding in the apolipoprotein E-knockout mouse: model characterization and effects of pravastatin treatment.* Circulation, 2005. 111(11): p. 1422-30.
11. Sasaki, T., et al., *A simple method of plaque rupture induction in apolipoprotein E-deficient mice.* Arterioscler Thromb Vasc Biol. 2006. 26(6): p. 1304-9.
12. Dimastromatteo, J., et al., *In vivo molecular imaging of atherosclerotic lesions in ApoE−/− mice using VCAM-1-specific, 99mTc-labeled peptidic sequences.* J Nucl Med, 2013. 54(8): p. 1442-9.
13. O'Brien, K. D., *Vascular Cell Adhesion Molecule-1 Is Expressed in Human Coronary Atherosclerotic Plaques.* The American Socciety for Clinical Investigation, 1993.
14. Sadeghi, M. M., *The pathobiology of the vessel wall: implications for imaging.* J Nucl Cardiol, 2006. 13(3): p. 402-14.
15. Willem J. M. Mulder, F. A. J., Zahi A. Fayad, Matthias Nahrendorf, *Imaging and Nanomedicine in Inflammatory Atherosclerosis.* Atherosclerosis. 2014. 6(239).
16. Sadeghi, M. M., et al., *Imaging atherosclerosis and vulnerable plaque.* J Nucl Med, 2010. 51 Suppl 1: p. 51S-65S.
17. van Leeuwen, M., et al., *Accumulation of myeloperoxidase-positive neutrophils in atherosclerotic lesions in LDLR−/− mice.* Arterioscler Thromb Vasc Biol, 2008. 28(1): p. 84-9.
18. Hong, S. N., et al., *Atherosclerotic biomarkers and aortic atherosclerosis by cardiovascular magnetic resonance imaging in the Framingham Heart Study.* J Am Heart Assoc. 2013. 2(6): p. e000307.
19. Horst, E., et al., *Expression of the leucocyte integrin LFA-1 (CD11a/CD18) and its ligand ICAM-1 (CD54) in lymphoid malignancies is related to lineage derivation and stage of differentiation but not to tumor grade.* Leukemia, 1991. 5(10): p. 848-53.
20. Yee, N. K., *Self-Regeneration of Stereocenters: A Practical Enantiospecific Synthesis of LEA-1 Antagonist BIRT-377.* 2000.
21. Kelly, T. A., *Cutting Edge: A Small Molecule Antagonist of LFA-1-Mediated Cell Adhesion.* The Journal of Immunology, 2015.
22. Shaw, S. K., et al., *Coordinated redistribution of leukocyte LFA-1 and endothelial cell ICAM-1 accompany neutrophil transmigration.* J Exp Med, 2004. 200(12): p. 1571-80.
23. Silvola, J. M. U., et al., *Uptake of (68)gallium in atherosclerotic plaques in LDLR(−/−)ApoB(100/100) mice.* Ejnmmi Research, 2011. 1.
24. Rahul B. Poria, J. P. N., Tamara L. Anderson, 2 Jack Erion, Carston R. Wagner, Jeffrey B. Arterburn, and Richard S. Larson6, *Characterization of a Radiolabeled Small Molecule Targeting Leukocyte Function Associated Antigen-1 Expression in Lymphoma and Leukemia.* Cancer Biotherapy & Radiopharmaceuticals. 2006.
25. Paffett, M. L., et al., *Ozone Inhalation Impairs Coronary Artery Dilation via Intracellular Oxidative Stress: Evidence for Serum-Borne Factors as Drivers of Systemic Toxicity.* Toxicol Sci, 2015. 146(2): p. 244-53.
26. Herrington, W., et al., *Epidemiology of Atherosclerosis and the Potential to Reduce the Global Burden of Atherothrombotic Disease.* Circ Res, 2016. 118(4): p. 535-46.
27. Burtea, C., et al., *Development of a magnetic resonance imaging protocol for the characterization of atherosclerotic plaque by using vascular cell adhesion molecule-1 and apoptosis-targeted ultrasmall superparamagnetic iron oxide derivatives.* Arterioscler Thromb Vasc Biol. 2012. 32(6): p. e36-48.
28. Collins, R. G., et al., *P-Selectin or intercellular adhesion molecule (ICAM)-1 deficiency substantially protects against atherosclerosis in apolipoprotein E-deficient mice.* J Exp Med, 2000. 191(1): p. 189-94.
29. Anderson, M. E. and T. J. Siahaan, *Targeting ICAM-1/LFA-1 interaction for controlling autoimmune diseases: designing peptide and small molecule inhibitors.* Peptides, 2003. 24(3): p. 487-501.
30. Wang, X. J., et al., *Efficient synthesis of a small molecule, nonpeptide inhibitor of LFA-1.* Org Lett, 2010. 12(19): p. 4412-5.
31. Vestweber. D., *Adhesion and signaling molecules controlling the transmigration of leukocytes through endothelium.* Immunological Reviews, 2007.
32. Tabdanov, E., et al., *Regulation of Immune Synapse Cytoskeleton Mechanics by CD3 and LFA1.* Biophysical Journal, 2011. 100(3): p. 34-35.
33. Riou, L. M., et al., *Pre-clinical and clinical evaluation of nuclear tracers for the molecular imaging of vulnerable atherosclerosis: an overview.* Curr Med Chem. 2009. 16(12): p. 1499-511.
34. Perales, J. L. G., *Blood volume analysis by radioisotopic dilution techniques: State of the art.* Applied Radiation and Isotopes, 2015. 96: p. 71-82.
35. Otsuki, H., et al., *Comparison of iron-59, indium-111, and gallium-69 transferrin as a macromolecular tracer of vascular permeability and the transferrin receptor.* J Nucl Med, 1989. 30(10): p. 1676-85.
36. Moos, M. P., et al., *The lamina adventitia is the major site of immune cell accumulation in standard chow-fed apolipoprotein E-deficient mice.* Arterioscler Thromb Vasc Biol, 2005. 25(11): p. 2386-91.
37. Ramot, Y., et al., *Clinical and pathological manifestations of cardiovascular disease in rat models: the influence of acute ozone exposure.* Inhal Toxicol, 2015. 27 Suppl 1: p. 26-38.
38. Katakami, N., *Utility of Carotid Wall Shear Stress as a Predictor of Coronary Atherosclerosis.* J Atheroscler Thromb, 2016. 23(3): p. 290-1.
39. Meng, H. et al., [*Feasibility of targeted magnetic resonance imaging on visualizing tenascin-C expression in atherosclerosis plaque in high-fat diet fed ApoE(−/−) mice*]. Zhonghua Xin Xue Guan Bing Za Zhi, 2016. 44(4): p. 342-7.
40. Mata. P., et al., [*Familial combined hyperlipidemia: consensus document*], Semergen, 2014. 40(7): p. 374-80.

41. Abd El-Aziz. T. A. and R. H. Mohamed, *LDLR, ApoB and ApoE genes polymorphisms and classical risk factors in premature coronary artery disease.* Gene. 2016.

The invention claimed is:

1. A method of diagnosing the existence of a ICAM-1/LFA-1 mediated disease or condition in tissue of a patient comprising administering to said patient an effective amount of at least one compound according to the chemical structure:

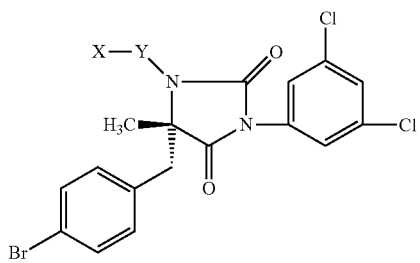

Where Y is a chemical linker which links the nitrogen to a chelate group or tricarbonyl complex X, wherein X Incorporates or complexes with a radioisotope, or a pharmaceutically acceptable salt thereof;
measuring the amount of said compound which binds to said tissue in said patient; and comparing the measurement obtained in said measuring step with a standard from uninfected tissue or infected tissue, wherein said measurement obtained from said patient is compared to said standard(s) and said comparison is determined to be indicative of the existence or the absence of a disease or condition in said tissue,
wherein said disease state or condition is atheroma, atherothrombosis or a combination of atheroma and atherothrombosis.

2. The method according to claim 1 wherein X incorporates a radioisotope selected from the group consisting of $^{90}$Y, $^{111}$In, $^{177}$Lu, $^{225}$Ac, $^{209}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{186}$Re, $^{99m}$Tc and mixtures thereof.

3. The method according to claim 1 wherein Y is a —(CH$_2$)$_n$NH— group, where n is from 0.2 to 4, preferably 4 and X is a chelate group.

4. The method according to claim 1 wherein said chelate group is 1,4,7,10-tetraazacyclododecane-1,4,7,10-tetraacetic acid (DOTA).

5. The method according to claim 1 wherein said radioisotope is $^{212}$Bi, $^{213}$Bi, $^{212}$Pb, $^{177}$Lu, $^{225}$Ac, $^{68}$Ga, $^{67}$Ga, $^{66}$Ga, $^{86}$Y, $^{90}$Y, or $^{111}$In.

6. The method according to claim 1 wherein said radioisotope is $^{68}$Ga or $^{111}$In.

7. The method according to claim 1 wherein said compound is represented by the chemical structure:

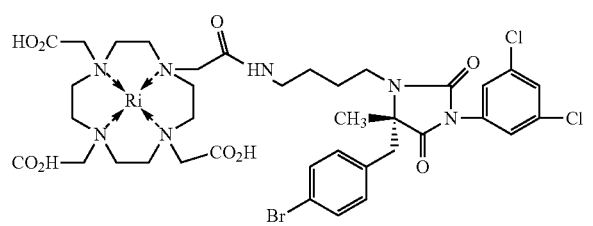

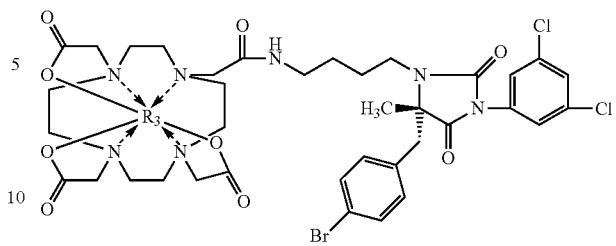

Where Ri is a radioisotope selected from the group consisting of $^{86}$Y, $^{90}$Y, $^{111}$In, $^{177}$Lu, $^{225}$Ac, $^{209}$Bi, $^{212}$Bi, $^{213}$Bi, $^{66}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{89}$Zr, $^{203}$Pb, $^{209}$Pb, $^{212}$Pb, $^{166}$Ho, $^{153}$Pm, $^{201}$Tl, $^{188}$Re, $^{186}$Re, $^{99m}$Tc and mixtures thereof, or a pharmaceutically acceptable salt thereof.

8. The method according to claim 1 wherein said compound is

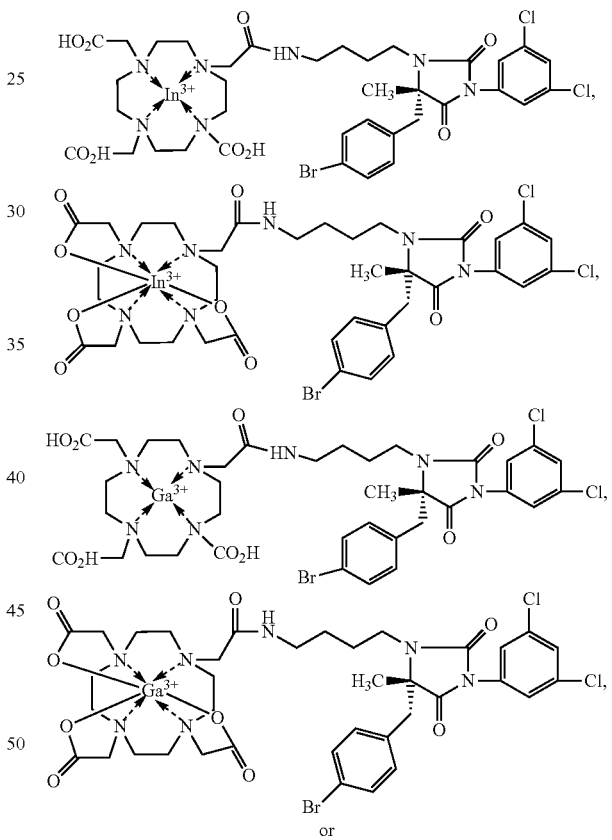

a pharmaceutically acceptable salt thereof.

9. The method according to claim 1 wherein said disease or condition is atheroma or atherothrombosis.

10. The method according to claim 9 wherein the atheroma or atherothrombosis is diagnosed by determining the extent of inflammation of atherosclerotic plaque in vascular tissue.

11. The method according to claim 10 wherein said vascular tissue is an artery or arteriole.

12. The method according to claim 11 wherein said blood vessel is an artery or arteriole in the heart, an aortic arch, descending aorta, a carotid artery, a femoral artery or, arteriole, a profunda femoral artery or arteriole, a renal artery or arteriole, a hypogastric artery or arteriole, an ilial artery or arteriole, a popliteal fossal artery or arteriole, a peroneal artery or arteriole, an anterior tibial artery, a posterior tibial artery, an anterior dorsalis pedis artery or arteriole, an abdominal aorta, a celiac artery, a gastric artery, a hepatic artery, a splenic artery, a subclavian artery, an axillary artery, a brachial artery, a radial artery, an ulnar artery, a thoracic aorta, a superior mesenteric artery or an inferior mesenteric artery of a patient.

13. A method of monitoring the treatment of a ICAM-1/LFA-1 mediated disease or condition in tissue of a patient comprising administering to said patient undergoing a course of treatment for said disease or condition an effective amount of at least one compound according to the chemical structure:

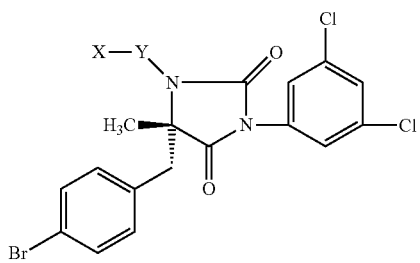

Where Y is a chemical linker which links the nitrogen to a chelate group or tricarbonyl complex X, wherein X incorporates or complexes with a radioisotope, or a pharmaceutically acceptable salt thereof;

measuring the amount of said compound which binds to said tissue in said patient at two different times or more during treatment; and comparing the measurements obtained in said measuring step at said different times with a standard from normal tissue and/or tissue impacted by said disease state and/or condition, wherein said measurements obtained from said patient are compared to said standard(s) and optionally, to each other, such that said comparison is indicative of the progress or absence of progress in the treatment of said disease or condition wherein said disease or condition is atheroma, atherothrombosis or a combination of atheroma and atherothrombosis.

14. The method according to claim 13 wherein said chelate group is 1,4,7,10-tetraazacyclododecane-1,4,7,10-tetraacetic acid (DOTA).

15. The method according to claim 13 wherein said compound is

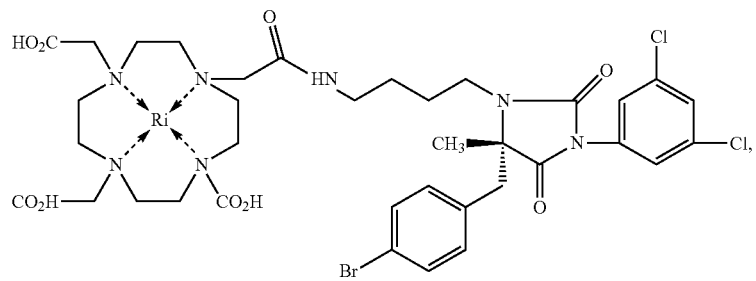

a pharmaceutically acceptable thereof, where Ri is a radioisotope selected from the group consisting of $^{86}$Y, $^{90}$Y, $^{111}$In, $^{177}$Lu, $^{225}$Ac, $^{209}$Bi, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{89}$Zr, $^{203}$Pb, $^{209}$Pb, $^{212}$Pb, $^{166}$Ho, $^{153}$Pm, $^{201}$Tl, $^{188}$Re, $^{186}$Re, $^{99m}$Tc and mixtures thereof.

16. The method according to claim 13 wherein said compound is

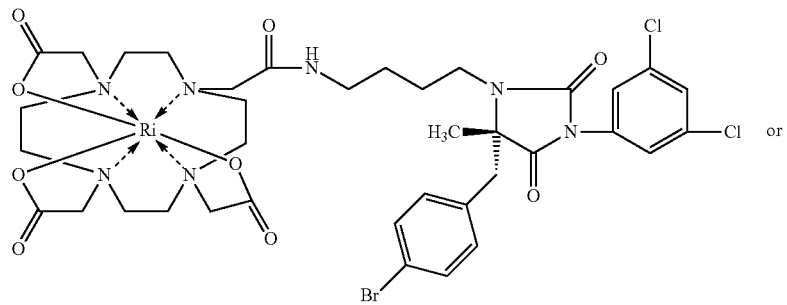

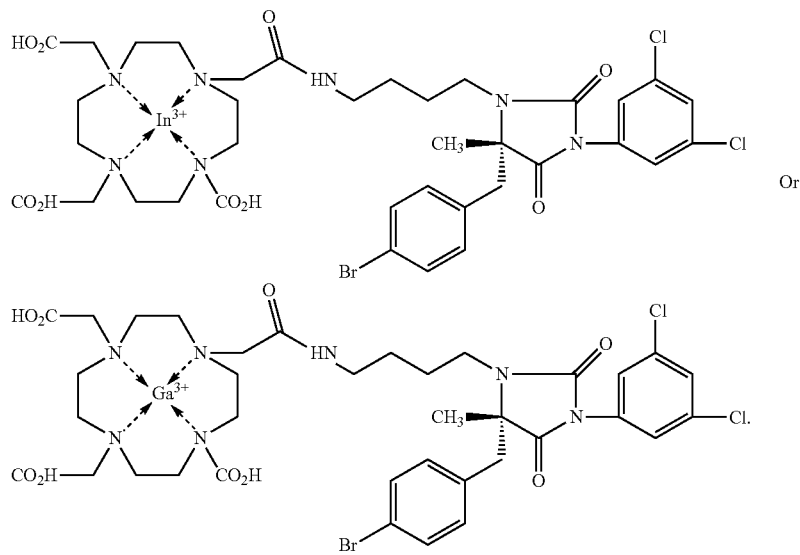

17. The method according to claim 13 wherein said atheroma or atherothrombosis is diagnosed by determining the extent of inflammation of atherosclerotic plaque in vascular tissue.

18. The method according to claim 17 wherein said vascular tissue is an artery or arteriole.

19. The method according to claim 18: wherein said blood vessel is an artery or arteriole of the heart, an aortic arch, descending aorta, a carotid artery, a femoral artery or arteriole, a profunda femoral artery or arteriole, a renal artery or arteriole, a hypogastric artery or arteriole, an ilial artery or arteriole, a popliteal fossal artery or arteriole, a peroneal artery or arteriole, an anterior tibial artery, a posterior tibial artery, an anterior dorsalis pedis artery or arteriole, an abdominal aorta, a celiac artery, a gastric artery, a hepatic artery, a splenic artery, a subclavian artery, an axillary artery, a brachial artery, a radial artery, an ulnar artery, a thoracic aorta, a superior mesenteric artery or an inferior mesenteric artery of a patient.

20. A method of treating a ICAM-1/LFA-1 mediated disease or condition in tissue of a patient in heed wherein said disease is atherothrombosis comprising administering to said patient an effective amount of at least one compound according to the chemical structure:

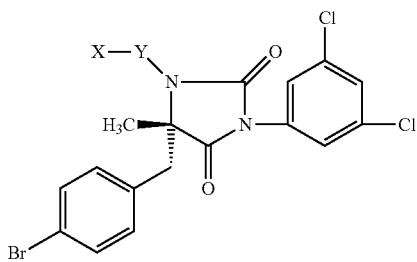

Where Y is a chemical linker which links the nitrogen to a chelate group or tricarbonyl complex X, wherein X incorporates or complexes with a radioisotope, or a pharmaceutically acceptable salt thereof.

* * * * *